United States Patent
Amigoni et al.

(10) Patent No.: US 10,155,869 B2
(45) Date of Patent: Dec. 18, 2018

(54) POLYMERISED CERIUM OXIDE NANOPARTICLES IN AN ACTIVE OR BIOACTIVE NETWORK, PROTECTIVE TOPICAL TREATMENTS, METHODS FOR PREPARATION THEREOF AND USES THEREOF

(71) Applicants: UNIVERSITE NICE SOPHIA ANTIPOLIS, Nice (FR); CENTRE NATIONAL DE LA RECHERCHE SCIENTIFIQUE, Paris (FR); UNIVERSITE D'ORLEANS, Orléans (FR)

(72) Inventors: Sonia Amigoni, Nice (FR); Denis Josse, Vaulnays le Haut (FR); Thierry Devers, Chartres (FR); Arnaud Zenerino, Blausasc (FR); Frédéric Guittard, Nice (FR); Elisabeth Taffin de Givenchy, Nice (FR); Cécile Bignon, Nice (FR)

(73) Assignees: UNIVERSITE NICE SOPHIA ANTIPOLIS, Nice (FR); CENTRE NATIONAL DE LA RECHERCHE SCIENTIFIQUE, Paris (FR); UNIVERSITE D'ORLEANS, Orléans (FR)

( * ) Notice: Subject to any disclaimer, the term of this patent is extended or adjusted under 35 U.S.C. 154(b) by 0 days.

(21) Appl. No.: 14/906,133

(22) PCT Filed: Jul. 18, 2014

(86) PCT No.: PCT/FR2014/000167
§ 371 (c)(1),
(2) Date: Jan. 19, 2016

(87) PCT Pub. No.: WO2015/007961
PCT Pub. Date: Jan. 22, 2015

(65) Prior Publication Data
US 2016/0152832 A1 Jun. 2, 2016

(30) Foreign Application Priority Data
Jul. 18, 2013 (FR) .................................... 13 01712

(51) Int. Cl.
*C09C 3/10* (2006.01)
*A61Q 19/00* (2006.01)
(Continued)

(52) U.S. Cl.
CPC .............. *C09C 3/10* (2013.01); *A61K 8/0241* (2013.01); *A61K 8/19* (2013.01); *A61K 8/8152* (2013.01);
(Continued)

(58) Field of Classification Search
CPC ...... A61Q 17/00; A61Q 19/00; A61K 8/0241; A61K 8/19; A61K 2800/413; A61K 2800/48; A61K 2800/548
See application file for complete search history.

(56) References Cited

U.S. PATENT DOCUMENTS 5,607,979 A 3/1997 McCreery
6,080,415 A * 6/2000 Simon .................. A61K 8/29
424/400

(Continued)

FOREIGN PATENT DOCUMENTS

EP 2 202 277 A1 6/2010
GB 2 314 020 A 12/1997
(Continued)

OTHER PUBLICATIONS

Zhang et al., "Galenical principles in skin protection", Curr. Probl. Dermatol., 2007, 34, 11-18; in English; cited in the Specification.
(Continued)

*Primary Examiner* — Jianfeng Song
(74) *Attorney, Agent, or Firm* — Westerman, Hattori, Daniels & Adrian, LLP telechelic comb ∿∿ = Intermolecular associations

(57) ABSTRACT

The invention concerns a compound formed by functionalized micro- or nanoparticles associated covalently with rheology-modifying polymers. The invention is characterized in that the functionalized micro- or nanoparticles are functionalized micro- or nanoparticles of cerium oxide ($CeO_2$) having a nominal diameter of between 1 and 1500 nm. The rheology-adapting or -modifying polymers are selected from among non-associative or associative polymers. The invention is used in skin protection or decontamination.

19 Claims, 7 Drawing Sheets

(51) Int. Cl.

| | |
|---|---|
| A61K 8/81 | (2006.01) |
| A61K 31/78 | (2006.01) |
| A61K 9/00 | (2006.01) |
| A61K 9/51 | (2006.01) |
| A61K 33/00 | (2006.01) |
| C01F 17/00 | (2006.01) |
| A61Q 17/00 | (2006.01) |
| A61K 8/02 | (2006.01) |
| A61K 8/19 | (2006.01) |
| A61K 9/50 | (2006.01) |
| C07F 7/18 | (2006.01) |
| B82Y 30/00 | (2011.01) |
| B82Y 5/00 | (2011.01) |

(52) U.S. Cl.
CPC .......... *A61K 9/0014* (2013.01); *A61K 9/5026* (2013.01); *A61K 9/5115* (2013.01); *A61K 9/5138* (2013.01); *A61K 31/78* (2013.01); *A61K 33/00* (2013.01); *A61Q 17/00* (2013.01); *A61Q 19/00* (2013.01); *C01F 17/0043* (2013.01); *C07F 7/1804* (2013.01); *A61K 2800/413* (2013.01); *A61K 2800/48* (2013.01); *A61K 2800/548* (2013.01); *A61K 2800/61* (2013.01); *A61K 2800/614* (2013.01); *B82Y 5/00* (2013.01); *B82Y 30/00* (2013.01); *C01P 2004/64* (2013.01); *C01P 2006/60* (2013.01)

(56) References Cited

U.S. PATENT DOCUMENTS

| | | | |
|---|---|---|---|
| 8,333,993 | B1 | 12/2012 | Perez et al. |
| 2002/0192476 | A1 | 12/2002 | Kambe et al. |
| 2003/0031438 | A1 | 2/2003 | Kambe et al. |
| 2004/0022867 | A1 | 2/2004 | Tucker et al. |
| 2009/0076207 | A1 | 3/2009 | Destarac et al. |
| 2010/0209710 | A1 | 8/2010 | Izu et al. |
| 2012/0142808 | A1 | 6/2012 | Izu et al. |
| 2012/0213854 | A1 | 8/2012 | Fetzer |
| 2014/0030339 | A1 | 1/2014 | Leblanc et al. |
| 2014/0147726 | A1 | 5/2014 | Toyoda |

FOREIGN PATENT DOCUMENTS

| | | |
|---|---|---|
| JP | H02-99974 A | 4/1990 |
| JP | H05-323678 A | 12/1993 |
| JP | 2004-524396 A | 8/2004 |
| JP | 2004-331883 A | 11/2004 |
| JP | 2004-537767 A | 12/2004 |
| JP | 2009-102570 A | 5/2009 |
| KR | 10-2012-0125999 A | 11/2012 |
| WO | 02058928 A1 | 8/2002 |
| WO | 03013846 A1 | 2/2003 |
| WO | 2006/117476 A1 | 11/2006 |
| WO | 2011/018939 A1 | 2/2011 |
| WO | 2012136607 A1 | 10/2012 |
| WO | 2013005796 A1 | 1/2013 |

OTHER PUBLICATIONS

Koper et al., "Development of reactive topical skin protectants against sulfur mustard and nerve agents", J. Appl. Toxicol., 1999, 19, 59-70; in English; cited in the Specification.

Saxena et al., "Removal of sulphur mustard, sarin and simulants on impregnated silica nanoparticles", J. Hazard. Mater., 2012, 211-212, 226-232; in English; cited in the Specification.

International Search Report and Written Opinion dated Nov. 19, 2014 issued in corresponding application No. PCT/FR2014/000167; w/ English partial translation and partial machine translation (17 pages).

Office Action dated Dec. 13, 2016 in co-pending U.S. Appl. No. 14/769,327; with PTO892; without returned SB08 (11 pages) (U.S. Pat. No. 8,333,993 cited in the Office Action is not listed in this IDS since it was previously listed in the IDS filed Jan. 19, 2016).

Final Office Action dated Jun. 23, 2017 in co-pending U.S. Appl. No. 14/769,327; without returned SB08 (11 pages).

International Search Report dated Jul. 22, 2014, issued in counterpart application No. PCT/FR2014/000043 of co-pending U.S. Appl. No. 14/769,327 (in English) (3 pages) (U.S. Pat. No. 5607979 and GB2314020 cited in the Specification of the co-pending application are not listed in this IDS since they were listed in the IDS filed Jan. 19, 2016 in this application).

Al-Sagheer, et al., "Visco-elastic properties of chitosantitania nanocomposites", Carbohydrate Polymers, Feb. 21, 2011, vol. 85, No. 2, pp. 356-362; cited in ISR of co-pending U.S. Appl. No. 14/769,327 (in English).

Le Chatelier-Brunet, "Synthèse et caractérisation de polymères amphiphiles trés hydrophobes anioniques et application au contrôle de la rhéologie de fluides complexes", May 30, 2005, Universite Paris VI; cited in ISR of co-pending U.S. Appl. No. 14/769,327 (w/ English machine translation) (341 pages).

Hwang, et al., "Rheological properties of chitosan solutions", Korea-Australia Rheology Journal, Dec. 2000, vol. 12, No. 3/4, pp. 175-179, cited in ISR of co-pending U.S. Appl. No. 14/769,327 (in English).

Japanese Office Action dated Oct. 17, 2017 in Japanese application No. 2015-558522, counterpait of co-pending U.S. Appl. No. 14/769,327 (with English machine translation; 6 pages).

Japanese Office Action dated Mar. 13, 2018 in counterpart Japanese application No. 2016-526671 (with machine ranslation, 10 pages) (D1 WO2012/136607, D6 JP2004-331883, D7 JP2004-524396, D8 JP2004-537767 cited in the Japanese Office Action are not listed in this IDS since they were listed in the IDS filed Dec. 29, 2017; D3 U.S. Pat. No. 8,333,993 cited in the Japanese Office Action is not listed in this IDS since it was listed in the IDS filed Jan. 19, 2016; D4 JP2010-155934.

Asati et al., "Oxidase-Like Activity of Polymer-Coated Cerium Oxide Nanoparticles", Angew. Chem. 2009, 48, 2308-2312 (in English).

European Office Action dated Aug. 20, 2018 in counterpart application No. EP 14758589.7 (with English machine translation, 13 pages).

Bignon, "Nanoparticules en réseau pour la protection cutanée" ["Nanoparticles in network for skin protection"], Thesis, University Nice Sophia Antipolis, France, Nov. 10, 2015, pp. 1, 57, from the Internet (retrieved Aug. 4, 2018) (with English machine-translation; cited in the EP Office Action dated Aug. 20, 2018; available at https://tel.archives-ouvertes.fr/tel-01271303; total 6 pages).

Zenerino, "Nanoparticules polymérisées en réseau actif ou bioactif pour la protection ou la décontamination" ["Polymerised nanoparticles in active or bioactive network for protection or decontamination"], Thesis, University Nice Sophia Antipolis, France, Oct. 1, 2012, pp. 1-195 (with English machine-translation; cited in the EP Office Action dated Aug. 20, 2018; total 304 pages).

(56) References Cited

OTHER PUBLICATIONS

Clément et al., "Toxicity assessment of silica nanoparticles, functionalised silica nanoparticles, and HASE-grafted silica nanoparticles", Science of the Total Environment, vol. 450-451, Mar. 5, 2013, pp. 120-128 (in English; cited in the EP Office Action dated Aug. 20, 2018).

Zenerino et al., "Homogeneous dispersion of SiO2 nanoparticles in an hydrosouble polymeric network", Reactive and Functional Polymers, Elsevier, Amsterdam, The Netherlands, vol. 73, No. 8, Apr. 20, 2013, pp. 1065-1071 (in English; cited in the EP Office Action dated Aug. 20, 2018).

Office Action dated Sep. 17, 2017 in co-pending U.S. Appl. No. 14/769,327 (without returned SB08; 10 pages) (US20140030339 cited in the Office Action is not listed in this IDS since it was already listed in the IDS filed Nov. 11, 2013).

\* cited by examiner

POLYMERISED CERIUM OXIDE NANOPARTICLES IN AN ACTIVE OR BIOACTIVE NETWORK, PROTECTIVE TOPICAL TREATMENTS, METHODS FOR PREPARATION THEREOF AND USES THEREOF

This invention relates to hybrid organic/inorganic compounds formed by functionalised cerium oxide ($CeO_2$) micro- or nanoparticles grafted covalently onto rheology-modifying polymers. More particularly, the invention relates to functionalised amine cerium oxide micro- or nanoparticles, grafted to polymers to form an active or bioactive lattice. The invention also relates to protective topical treatments comprising them, their synthesis methods and uses particularly for skin protection or decontamination.

There may be several types of contamination by biological or chemical risk agents. Biological risk agents are usually bacteria, viruses or toxins. Chemical risk agents are usually organophosphate neurotoxins or vesicants.

Many studies have been carried out to protect human beings starting when chemical terrorism and bioterrorism first existed. Wearing a protective suit is compulsory during interventions, for example following an act of terrorism or during the use of toxins by the army. This type of suit must also be used in agricultural environments and in some industries. For example, the use of hazardous pesticides can contaminate the organism and cause severe lesions or even death of the user. The major problem with protective suits is that they cause modification to the operational capabilities of persons doing the work and a reduction in their sensorial capabilities (view, hearing, manual dexterity, etc.). They also quickly reach usage limits because they may be badly adjusted or torn and thus expose the skin to toxins.

For all the above reasons, new protection means have to be found to restore all or some of their faculties to their users. It is important to identify risk agents and their properties and mode of penetration into the skin, before defining what protection means will be used.

Toxins can be classified according to several criteria such as their volatility, military use or their hemotoxic, vesicant, suffocating, neurotoxic, incapacitating, neutralising effects.

At the present time, there is a great deal of interest in protection against vesicants and organophosphates that form the main chemical threat. Vesicants are represented mainly by the sulphur or nitrogen yperites and more modestly by lewisite and phosgene oxime. Organophosphates (OPs) include pesticides (POP) and organophosphate neurotoxins (NOP). Most POPs are phosphates or phosphorothioates containing O,O-dimethyl or O,O-diethyl substitutes on the phosphorus atom. They are usually indirect inhibitors of cholinesterases, in other words they only become active after metabolic transformation; S-oxidation of the P=S bond. This results in a longer latency between exposure and the development of intoxication symptoms. Organophosphate pesticides have replaced organochlorinated compounds that were highly remanent despite the higher toxicity of POPs. The first compounds such as parathion (O,O-diethyl and O-p-nitrophenyl phosphorothioate), malathion (S-(1,2-dicarbethoxyethyl and O,O-dimethyl di-thiophosphate) and paraoxon (diethyl p-nitrophenyl phosphate) are powerful cholinesterase inhibitors. Organophosphate pesticides are extremely toxic and cause severe intoxications, particularly in agricultural environments. The World Health Organisation (WHO) has estimated that there are a million serious poisonings due to pesticides every year, and approximately 220,000 deaths. The risk of intoxication by pesticides is high due to frequent contact when spraying pesticides on the ground or from the air and while handling.

The first organophosphate neurotoxins (NOPs) synthesised for use as chemical weapons for warfare were G agents. They include particularly the GA agent or Tabun, the GB agent or Sarin and the GD agent or Soman. These are esters of fluorophosphonic or phosphoramidic acid derivatives. V agents are other organophosphate neurotoxins (NOP).

Exposure to excessive concentrations of such agents can cause a set of symptoms typical of hypercholinergy: intense bronchial, salivary, ocular and intestinal secretions, sweating, bradycardia, muscular contractions, trembling, paralysis, loss of conscience, convulsions, malfunction of the respiratory system, that can lead to death.

Thus, the best way of preventing percutaneous toxicity of chemicals is to never allow them to come into contact with the skin.

As mentioned above, skin contamination is prevented principally by wearing protection such as a suit, a mask and gloves. However, there are some zones that remain exposed to these agents during movements of a human being or due to a defect in the protection, for example if the protective equipment is badly adjusted or unsuitable.

Furthermore, contamination can also be transferred to the skin during the undressing phase.

Therefore, there is a need to develop other means of protection that are very well tolerated by their user, easy to use, resistant to the external environment and that do not hinder the wearer.

To achieve this, the use of protective topical treatments provides alternative or complementary means of protection against irritants and environmental aggression such as for example microorganisms, chemicals such as vesicants and organophosphate compounds.

Most products sold under the term "protective topical treatments" (TP) include simply emollient cosmetics and formulations that can potentially perform a barrier function facing aggressive chemicals. These topical treatments are intended for use in risk environments. Protective topical treatments are provided for domestic or professional use. They can thus be used:
- to prevent contact allergy with many metals such as nickel, cobalt, chromium, palladium and gold;
- as solar filters for filtration of UVA and UVB radiation;
- as insect repellents;
- for chemical protection against acids, bases, surfactants and organic solvents.

Protective topical treatments based on perfluorinated compounds provide good means of protecting the organism and are not difficult to use. Such topical treatments are described particularly in the document by Zhang J.; Smith E. W., Surber C.; Galenical principles in skin protection, Curr. Probl. Dermatol., 2007, 34, 11-18; and in documents U.S. Pat. No. 5,607,979, and GB 2 314 020.

However, such topical treatments do not degrade contaminants and their protective effect is limited particularly following exposures to chemical vapours.

A second generation of protective topical treatments has also been developed, consisting of incorporation of organic or inorganic active constituents that can neutralise chemical contaminants. Such topical treatments are described particularly in the document by Koper O.; Lucas E.; Klabunde K. J.; Development of reactive topical skin protectants against sulfur mustard and nerve agents, J. Appl. Toxinol., 1999, 19, 59-70; and in the document by Saxena A.; Srivastava A. K.; Singh B.; Goyal A.; Removal of sulphur mustard, sarin and simulants on impregnated silica nanoparticles, J. Hazard. Mater., 2012, 211-212, 226-232).

Their protective efficiency has been partially established but not optimised particularly due to the agglomeration of micro- and/or nanoparticulate active constituents.

Therefore, at the present time, there is a need to develop new protective topical treatments that are more efficient, that are not toxic or are only slightly toxic, easy to apply and that have a wide range of action against biological and/or chemical risk agents. Preferably, such protective topical treatments can destroy biological and/or chemical risk agents. Thus, these agents do not penetrate into the skin of the individual.

Furthermore, such topical treatments should ideally be applicable by simple, fast and inexpensive methods and they should have a uniform formulation.

This is the context in which the Applicant has developed a new concept consisting of grafting micro- or nanoparticles, particularly known for their neutralising effect on toxic and/or biological chemicals, onto polymers that in particular modify the rheology, facilitating the integration and homogeneous dispersion of micro- or nanoparticles in a topical formulation, but also by avoiding the repeated release of micro- or nanoparticles.

Thus, the solution to the stated problem is a compound composed of functionalised micro- or nanoparticles, associated covalently with rheology-modifying polymers, characterised in that:
  the functionalised micro- or nanoparticles are functionalised micro- or nanoparticles of cerium oxide ($CeO_2$) with a nominal diameter between 1 and 1500 nm;
  the rheology-modifying or adapting polymers are chosen from among non-associative polymers and associative polymers.

Surprisingly, as illustrated in Example 7, the Applicant has been able to demonstrate that compounds according to the invention can provide excellent protective topical treatments that limit transmembrane penetration of toxins such as paraoxon.

The second purpose of this invention is a topical protective treatment comprising a compound according to the invention, in a pharmaceutically and/or cosmetically acceptable milieu.

A third purpose of this invention is a compound or a topical protective treatment according to the invention for use as a medicine.

A fourth purpose of this invention is a compound or a topical protective treatment according to the invention for use in the prevention of skin irritations or allergies.

A fifth purpose of this invention is the use of a compound or a topical protective treatment according to the invention for skin protection or decontamination, particularly due to biological and/or chemical risk agents.

A sixth purpose of this invention is a method for synthesising a compound according to the invention including the following steps:
  mix a coupling agent with a catalyst;
  add the mix obtained to a solution of rheology-modifying or adapting polymers chosen from among non-associative polymers and associative polymers, in water;
  stir the reaction mix;
  add functionalised micro- or nanoparticles of cerium oxide ($CeO_2$) with a nominal diameter between 5 and 1500 nm, previously dispersed in an aqueous phase, to the reaction mix;
  purification of the reaction medium by dialysis; and
  recovery of the compound formed by one or several functionalised amine micro- or nanoparticles associated covalently with one or several rheology-modifying polymers.

Its final purpose is methods for synthesis of compounds according to the invention.

In particular, the previously described compounds and topical treatments can be synthesised using different methods, the main steps of which are described in examples 1 to 6.

The invention will be better understood after reading the non-limitative description given below with reference to the appended drawings in which.

Figure 1:
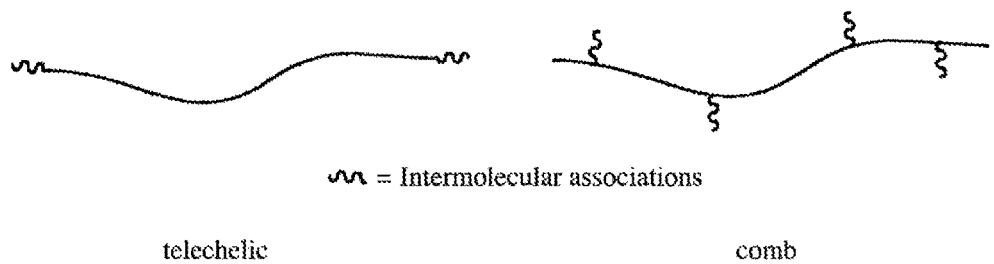
FIG. 1 is a diagrammatic view of telechelic type and comb type compounds.

The compound according to the invention is a compound formed by functionalised micro or nanoparticles covalently associated with rheology-modifying polymers, characterised in that:
  the functionalised micro- or nanoparticles are functionalised micro- or nanoparticles of cerium oxide ($CeO_2$) with a nominal diameter between 1 and 1500 nm;
  the rheology-modifying or adapting polymers are chosen from among non-associative polymers or associative polymers.

According to the invention, a nanoparticle is defined as being a nano-object for which all three dimensions are at the nanometric scale, in other words a particle for which the nominal diameter is less than 100 nm.

Preferably, the diameter of the nanoparticle according to the invention is between 1 and 50 nm. Also preferably, the diameter of the nanoparticle is between 5 nm and 25 nm.

A microparticle according to the invention is a microobject for which the three dimensions are at the micrometric scale, in other words a particle for which the nominal diameter is between 100 nm and 100,000 nm. Preferably, the microparticle according to the invention has a nominal diameter between 100 nm and 5000 nm. Also preferably, the nominal diameter of the microparticle is between 100 nm and 1500 nm.

Micro- or nanoparticles may be produced by various methods, particularly by chemical vapour phase synthesis, liquid phase synthesis, solid phase synthesis, mixed phase synthesis or by physicochemical methods such as evaporation/condensation.

According to one preferred embodiment of the invention, micro- or nanoparticles of cerium oxide or cerium dioxide ($CeO_2$) may be synthesised in a mixed medium using the sol-gel method. The principle of the sol-gel method is based on the use of a sequence of hydrolysis-condensation reactions at a moderate temperature close to ambient temperature, to prepare oxide lattices that can in turn be heat treated. The soluble metallic species can also contain organic constituents that can be adjusted depending on the application. The first step in sol-gel synthesis is hydroxylation of the metallic alkoxy that occurs during hydrolysis of the alkoxy group:

Step 1:
hydrolysis: $M'\text{-}OR' + H_2O \rightarrow M'\text{-}OH + R'OH$ where M' is cerium; and R' is an organic alkyl group containing 1 to 5 atoms of carbon, preferably from 2 to 3 atoms of carbon.

The hydroxy reactive groups are then generated. The solution obtained is called a sol. They are then modified by polycondensation reactions through two competitive mechanisms, namely the formation of an oxygen bridge (oxolation) or a hydroxo bridge (olation). This corresponds to the formation of the inorganic macromolecular lattice with elimination of water or alcohol:

Step 2:
Condensation:
Oxolation: $M'\text{-}OH + M'\text{-}OR' \rightarrow M'\text{-}O\text{-}M' + R'OH$ where M' and R' are as defined above, in other words M' is cerium; and R' is an organic alkyl group containing 1 to 5 atoms of carbon, preferably from 2 to 3 atoms of carbon.

Olation: $M'\text{-}OH + HO\text{-}M' \rightarrow M'(OH)_2M'$ where M' is Cerium.

The gel corresponds to the formation of a three-dimensional lattice of Van der Waals bonds.

Micro- or nanoparticles that can be used according to the invention preferably have a nominal average diameter between 1 and 1500 nm.

Advantageously, the nominal average diameter of micro- or nanoparticles of cerium oxide ($CeO_2$) is between 1 and 300 nm. Preferably, their nominal average diameter is between 5 and 150 nm. Also preferably, their nominal average diameter is between 8 and 10 nm.

The micro- or nanoparticles can be functionalised for example by primary or secondary amine functions, epoxy functions, alcohol functions or thiol functions.

Preferably, the micro- or nanoparticles of cerium oxide ($CeO_2$) are amine functionalised.

Figure 2:
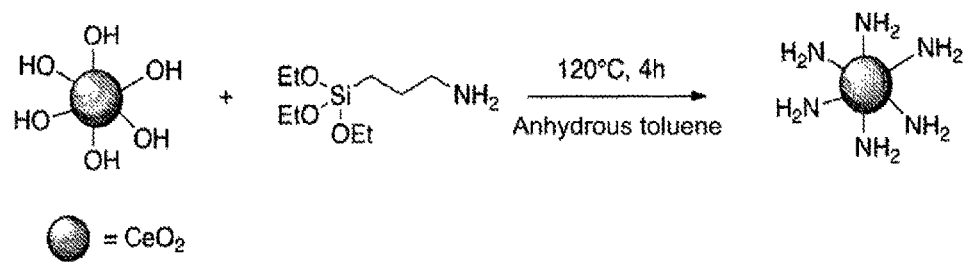
FIG. 2 illustrates functionalisation of cerium oxide nanoparticles by (3-aminopropyl) triethoxysilane in anhydrous toluene.

FIG. 2 contains a general diagram on amine functionalisation of micro- or nanoparticles.

Details of methods of synthesising cerium oxide nanoparticles are described in example 1.

Preferably, the content of amine functions on amine functionalised micro- or nanoparticles is between 0.1 and 10 meq/g of micro- or nanoparticles.

The number of NH2 functions obtained is in meq/g of micro- or nanoparticles and is calculated using the following equation:

$$\frac{\text{Number of } NH_2 \text{ functions}}{q} \left(\frac{Meq}{-}\right) = \frac{\% \, N \text{ by mass (determined by elementary analysis)}}{\text{Molar mass of nitrogen}} \times 100$$

Preferably, the content of amine functions on amine functionalised micro- or nanoparticles is between 0.1 and 4 meq/g of micro- or nanoparticles. Also preferably, the content of amine functions on micro- or nanoparticles is about 0.5 or 2.5 meq/g of micro- or nanoparticles.

As described above, the micro- or nanoparticles according to the invention are amine functionalised in order to react on acid functions of polymers.

Rheology-modifying or adapting polymers according to the invention are already used alone for their rheological properties in domains such as cosmetics and paint.

These are hydrocarbon or fluorocarbon polymers synthesised for example by polymerisation in emulsion.

They are then characterised by infrared (IR) using the KBr pellet method, by goniometry for dry deposits on a glass surface, but also in solution by Nuclear Magnetic Resonance (NMR) and rheology. Polymers according to the invention also contribute to stability of protective formulations or protective topical treatments.

Polymers that can be used fall into two different classes: non-associative polymers and associative polymers.

Non-associative polymers or emulsions that can swell in an alkali milieu for "Alkali-Swellable Emulsions" (ASE) that can be used according to the invention are already widely used alone as thickeners in latex coatings, paints and adhesives.

They are composed mainly of acrylic or methacrylic acid and C1-C4 alkyl acrylate monomers, preferably ethyl acrylate.

They are generally synthesised by polymerisation in emulsion in an acid aqueous medium (pH less than 4) and are obtained in the form of a colloidal suspension of polymers (or synthetic latexes). Acid functions of the copolymer are ionised in a basic environment that causes solubilisation and swelling of the polymer (increase in the hydrodynamic volume). Ethyl acrylate groups are sufficiently blocked to induce hydrophobic associations between polymer chains and to increase the viscosity.

Furthermore, non-associative ASE polymers can be optimised by cross-linking. The cross-linking phenomenon can physically densify the polymer lattice that reduces the possibility of molecule movements and therefore increases the viscosity.

Non-associative polymers according to the invention may include a hydrocarbon chain (ASE-H) and/or a fluorocarbon chain (ASE-F).

Preferably, non-associative ASE-H polymers satisfy the following general formula (I):

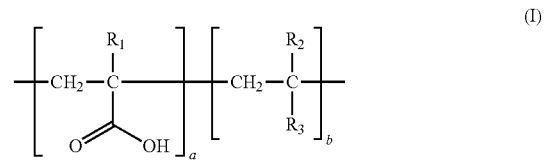

in which:
R1 and R2 represent a hydrogen atom or a —$CH_3$ methyl group;

R3 represents $[Q]_{d1}$-$(CH_2)_n$—H in which n is between 1 and 30, d1 is equal to 0 or 1, and Q is equal to —C(O)—O or —C(O)—NH—;
or
R3 represents $[Q]d2$-α, in which:
d2 is equal to 0 or 1;
Q is equal to —C(O)—O or —C(O)—NH—; and
α is equal to —C(CH$_3$)$_3$; —CH(CH$_3$)$_2$; —C(CH$_3$)$_2$—CH$_2$—C(CH$_3$)$_3$; —CN; —CH$_2$CH$_2$—N+(CH$_3$)$_2$(CH$_2$CO$_2^-$); —CH$_2$CH$_2$—NH—C(CH$_3$)$_3$; —CH$_2$CH$_2$—N(CH$_3$)$_2$; pyrrolidinone; caprolactam;
and in which indices a and b are integer numbers that may be identical or different, and are more than 1. Preferably, a is between 1 and 10,000 and b is between 1 and 20,000.

Throughout this description, polymers are composed of different monomers or macromers with given molar concentrations that vary as a function of the values of a, b and/or c. Obviously, chaining of the different monomers or macromers in the polymers obtained is variable and is not fixed in formulas (I), (II), (III), (V), (VI), (VII), and (VIII).

Also preferably, ASE polymers with a hydrocarbon chain (ASE-H) include acrylic and/or methacrylic acid and C1-C4 alkyl acrylate monomers.

Advantageously, ASE polymers with a hydrocarbon chain (ASE-H) include:
from 5 to 50 molar percent of acrylic acid and/or methacrylic acid;
from 50 to 95 molar percent of C1-C4 alkyl acrylates.

More preferably, the ASE-H polymers include the following monomers:
from 10 to 20 molar percent of methacrylic acid (AM);
from 80 to 90 molar percent of ethyl acrylate (AE).

ASE polymers with a hydrocarbon chain (ASE-H) have particularly advantageous thickening properties when the methacrylic acid/ethyl acrylate ratio is between 0.1 and 0.5. The most preferred ratio is 0.21.

As mentioned above, non-associative ASE polymers according to the invention may also include a fluorocarbon chain (ASE-F).

Preferably, non-associative ASE-F polymers satisfy the following general formula (II):

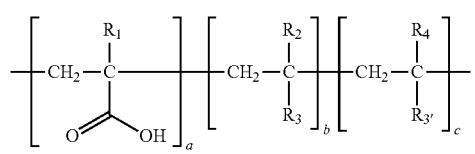

(II)

in which:
R1, R2 and R4 represent a hydrogen atom or a —CH$_3$ methyl group;
R3 represents $[Q]_{d1}$-$(CH_2)_n$—H in which n is between 1 and 30, d1 is equal to 0 or 1, and Q is equal to —C(O)—O or —C(O)—NH—;
or
R3 represents $[Q]_{d2}$-α, in which:
d2 is equal to 0 or 1;
Q is equal to —C(O)—O or —C(O)—NH—; and
α is equal to —C(CH$_3$)$_3$; —CH(CH$_3$)$_2$; —C(CH$_3$)$_2$—CH$_2$—C(CH$_3$)$_3$; —CN; —CH$_2$CH$_2$—N+(CH$_3$)$_2$CH$_2$CO$_2^-$); —CH$_2$CH$_2$—NH—C(CH$_3$)$_3$; —CH$_2$CH$_2$—N(CH$_3$)$_2$; pyrrolidinone; caprolactam;
R3' represents $[Q]_{d1}$-$(CH_2)_n$—$(CX_2)_p$X in which n is between 1 and 30, d1 is equal to 0 or 1, and Q is equal to —C(O)—O or —C(O)—NH—, X is a fluorine atom F and p is between 1 and 12;

and in which the indices a and c are integer numbers, identical or different, greater than 1 and b is greater than or equal to 0; a is preferably between 1 and 10,000, b is between 0 and 5000 and c is between 1 and 8000.

These ASE-F polymers are preferably composed of monomers:
of methacrylic acid (AM);
of 2,2,2-trifluoroethyl methacrylate (TFEM) or trifluoroethyl acrylate or 2-perfluorobutylethyl acrylate or 2-perfluorohexylethyl acrylate or 2-perfluorooctylethyl acrylate; and
C1-C4 alkyl acrylate, preferably ethyl acrylate (AE).

Introduction of a fluorocarbon chain for a cosmetic or pharmaceutical use can reduce adsorption of toxins on the surface.

Preferably, ASE polymers with a fluorocarbon chain (ASE-F) are composed of the following monomers:
from 20 to 75 molar percent of acrylic and/or methacrylic acid;
from 0 to 30 molar percent of C1-C4 alkyl acrylates; and
from 10 to 55 molar percent of 2,2,2-trifluoroethyl methacrylate (TFEM) or trifluoroethyl acrylate or 2-perfluorobutylethyl acrylate or 2-perfluorohexylethyl acrylate or 2-perfluorooctylethyl acrylate.

Also preferably, ASE polymers with a fluorocarbon chain (ASE-F) include methacrylic acid (AM), ethyl acrylate (AE) and 2,2,2-trifluoroethyl methacrylate (TFEM) monomers.

Advantageously, ASE polymers with a hydrocarbon chain (ASE-F) include:
from 50 to 60 molar percent of methacrylic acid (AM);
from 5 to 15 molar percent of ethyl acrylate (AE); and
from 30 to 40 molar percent of 2,2,2-trifluoroethyl methacrylate (TFEM).

Figure 3:
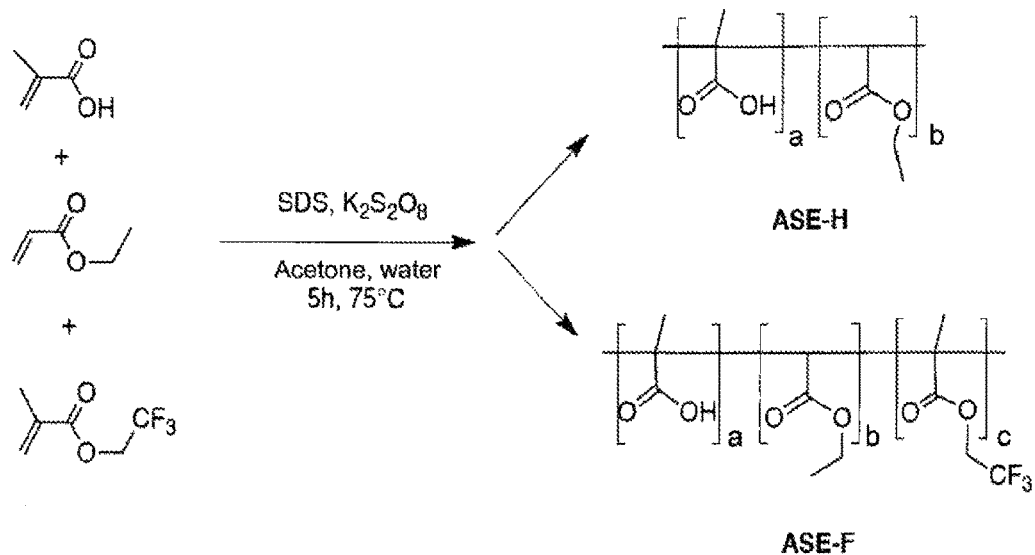
FIG. 3 illustrates a synthesis diagram for non-associative ASE-H and ASE-F polymers.

Even more preferably, ASE polymers with a fluorocarbon chain (ASE-F) have particularly advantageous thickening properties when the ratio of methacrylic acid (AM)/ethyl acrylate (AE) monomers is between 7 and 0.1. FIG. 3 shows the general formula of ASE-H and ASE-F polymers that can be used according to the invention. A method of synthesising ASE-H and ASE-F polymers is described in example 2 and is summarised in FIG. 3, in which the indices a, b and c are integer numbers that may be identical or different and are more than 1. Preferably, a is between 1 and 10,000; b is between 1 and 5,000 and c is between 1 and 8,000.

Associative polymers that can be used according to the invention are composed of a hydrophilic macromolecular structure on which hydrophobic groups are present. These hydrophobic groups are often alkyl bonds with short chains (between 1 and 6 carbon atoms) or long chains (with more than 6 carbon atoms) capable of forming aggregates, clusters, of the micellar type, starting from a concentration called the critical aggregation. These aggregates are called hydrophobic junctions.

At the present time, there are three types of different associative polymers marketed that can be used according to the invention. They are:
hydrophobically modified ethylene-oxide urethanes (HEUR);
cellulose derivatives; and
hydrophobically modified alkali-swellable emulsions (HASE).

These three types of polymers are classified in two categories of associative polymers depending on their molecular architecture:

1. so-called telechelic polymers; or
2. comb-type polymers.

FIG. 1 shows a diagrammatic view of telechelic type and comb type compounds. Telechelic polymers (HEUR) are linear chains of polymers containing hydrophobic groups at the end of the chain. Comb type polymers (cellulose derivatives and HASE polymers) are polymers containing hydrophobic long skeleton chains.

HASE polymers are usually copolymers of methacrylic acid (AM), ethyl acrylate (AE) and a quantity of hydrophobic groups that are monomers or macromers.

Despite the presence of hydrophobic groups that are long hydrocarbon chains, HASE polymers are soluble in an aqueous medium that makes them particularly attractive.

Like ASE polymers, HASE polymers are usually prepared by polymerisation in emulsion with low pH, that can give polymers with a molar mass between 300,000 and 1,800,000 g/mol.

The rheological properties of HASE polymers have shown that the viscosity depends strongly on the pH. In the pH range between 2.4 and 4.5, the polymer skeleton folds to form a compact coil due to the low solvent quality. The polymer solution is milky and consists of insoluble colloidal particles. At pH 6, the viscosity increases suddenly and remains constant until pH 11, carboxyl groups on the polymer skeleton dissolve and the solution becomes transparent. The polymer chain then resembles a polyelectrolyte that causes extension of the polymer skeleton due to mutual repulsion of carboxylates and an increase in the hydrodynamic volume. At the same time, a large number of inter and intramolecular associations are formed between the hydrophobic groups, which results in the construction of a lattice within the aqueous medium.

With a basic pH, HASE polymers combine the properties of polyelectrolytes and the properties of uncharged associative polymers. For a pH higher than 11, the viscosity slowly reduces due to the protective effect of the charge. Other factors may vary the dynamic nature of the polymer and the structure of HASE polymers, particularly such as the concentration of salts in the medium. When this concentration is high, the viscosity reduces significantly. The negative effect of adding salts may be compensated by the addition of a surfactant. The concentration of surfactant can vary the viscosity of the medium. Growth in the concentration by a non-ionic surfactant can increase the viscosity in the medium, while an anionic surfactant increases the viscosity up to a critical concentration at which it drops.

The viscosity of the medium can also be reduced when the temperature increases.

The use of a strong base (NaOH) to neutralise a HASE polymer causes degradation of the polymer after a period of four weeks (pH=9.5). The use of a slightly organic base (1-amino-1-methylpropanol) stabilises the rheological properties of the solution for six weeks (pH=9.5).

Monovalent neutralising agents can also be recommended. When a basic di- or trivalent molecule that thus has the capability of neutralising more than one carboxylic acid function, there may be a reduction in the capacity of the polymer to unwind and expand completely.

Finally, the addition of an organic solvent can reduce the viscosity of the medium by breaking hydrophobic associations within the aqueous medium and solubilising hydrophobic groups.

Preferably, polymers according to the invention are HASE polymers with hydrocarbon chain macromers (HASE-H-RH or HASE-F-RH) or a fluorocarbon chain (HASE-F-RF).

HASE associative polymers with macromers having a hydrocarbon chain (HASE-H-RH or HASE-F-RH) or a fluorocarbon chain (HASE-F-RF) according to the invention satisfy the following general formula (III):

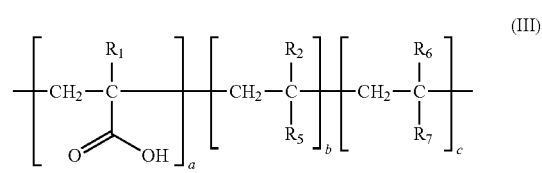

in which:
R1, R2 and R6 represent a hydrogen atom or a methyl group;
R5 represents $[Q]_{d1}$-$(CH_2)_n$—$(CX_2)_p$X in which n is between 1 and 30, d1 is equal to 0 or 1, and Q is equal to —C(O)—O or —C(O)—NH—; and
when X is a hydrogen atom, p is equal to 0;
when X is a fluorine atom, p is between 1 and 12; or
R6 represents $[Q]d2$-α in which:
d2 is equal to 0 or 1;
Q is equal to —C(O)—O or —C(O)—NH—; and
α is equal to —C(CH$_3$)$_3$; —CH(CH$_3$)$_2$; —C(CH$_3$)$_2$—CH$_2$—C(CH$_3$)$_3$; —CN; —CH$_2$CH$_2$—N+(CH$_3$)$_2$CH$_2$CO$_2$$^-$); —CH$_2$CH$_2$—NH—C(CH$_3$)$_3$; —CH$_2$CH$_2$—N(CH$_3$)$_2$; pyrrolidinone; caprolactam;
R7 represents $[Q']_{d3}$-$(OCH_2CH_2)_q$-$[Q'']_{d4}$-$(CH_2)_n(CX_2)_p$X in which Q' is equal to —CH$_2$, C(O), O—C(O) or —NH—C(O), n is between 1 and 30, q is between 1 and 150, d3 and d4 are equal to 0 and/or 1, Q'' is equal to —O—C(O) or —NH—C(O); and
when X is a hydrogen atom, p is equal to 0;
when X is a fluorine atom, p is between 1 and 12;
and in which the indices a and c are integer numbers, identical or different, greater than or equal to 1, and b is greater than or equal to 0.

Preferably, a is between 1 and 10,000; b is between 0 and 10,000 and c is between 1 and 5,000.

Preferably, the HASE-H-RH polymers with a hydrocarbon chain are composed of monomers of methacrylic acid (AM), C1-C4 alkyl acrylates and a macromer that is an ester with a general formula (IV):

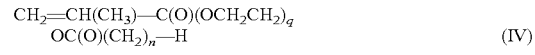

in which q is a number between 5 and 10 and n is between 6 and 30 carbon atoms.

Also preferably, the HASE-H-RH polymers include monomers of methacrylic acid (AM), ethyl acrylate (AE) and a macromer that is an ester with general formula (IV) as defined above, and therefore satisfy the following general formula (V):

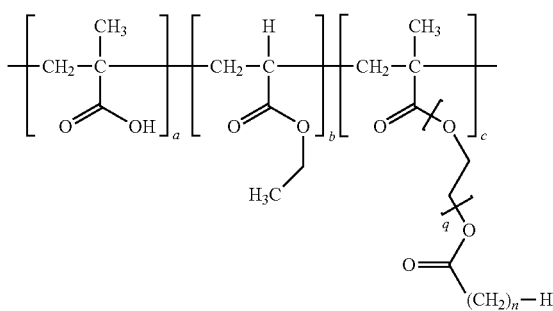

(V)

in which:
q is a number between 5 and 10;
n is between 1 and 30;
a and c are integer numbers, that may be identical or different that are greater than or equal to 1, b is greater than or equal to 0; preferably, a is between 1 and 10,000, b is between 0 and 10,000 and c is between 1 and 5,000.

Also preferably, HASE-H-RH polymers satisfy the general formula (V) and include:
5 to 85 molar percent of methacrylic acid (AM);
5 to 60 molar percent of ethyl acrylate (AE); and
1 to 90 molar percent of a macromer that is an ester with general formula (IV) defined above.

The particularly preferred HASE-H-RH polymers satisfy the formula (V) above, and are such that:
q is equal to 7 and n is equal to 6 carbon atoms (subsequently called HASE-H-RH4 polymer);
q is equal to 7 and n is equal to 8 carbon atoms (subsequently called HASE-H-RH6 polymer);
q is equal to 9 and n is equal to 10 carbon atoms (subsequently called HASE-H-RH8 polymer);

Alternately, according to the invention, the ethyl acrylate monomer (AE) of the HASE-H-RH polymer with formula (V) above may be replaced by a 2,2,2-trifluoroethyl methacrylate monomer (TFEM) and therefore corresponds to a HASE-F-RH polymer that satisfies the general formula (VI) given below:

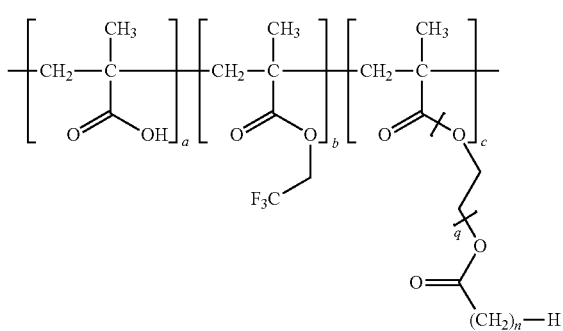

(VI)

in which:
q denotes a number between 5 and 10;
n is between 6 and 30 carbon atoms;
a and c are integer numbers that may be identical or different, greater than or equal to 1, and b is greater than or equal to 0; preferably, a is between 1 and 10,000, b is between 0 and 10,000, and c is between 1 and 5,000.

Also preferably, the HASE-F-RH polymers satisfy the general formula (VI) above and include:
from 30 to 85 molar percent of methacrylic acid (AM);
from 0 to 50 molar percent of 2,2,2-trifluoroethyl methacrylate (TFEM); and
from 1 to 90 molar percent of a macromer that is an ester with general formula (IV).

Particularly preferred HASE-F-RH polymers satisfy formula (VI) above, and are such that:
q is equal to 7 and n is equal to 6 carbon atoms (subsequently called HASE-F-RH4 polymer);
q is equal to 7 and n is equal to 8 carbon atoms (subsequently called HASE-F-RH6 polymer);
q is equal to 9 and n is equal to 10 carbon atoms (subsequently called HASE-F-RH8 polymer);

Advantageously, the Applicant has also demonstrated that substitution of hydrocarbon chains by fluorocarbon chains on the macromer is possible in an HASE skeleton.

By modifying its skeleton with fluorocarbon macromers in this way, the rheology-modifying polymer according to the invention can disperse micro- or nanoparticles while providing the hydrophobia and oleophobia necessary for protection against chemicals.

The structure of such HASE polymers with fluorocarbon chain (HASE-F), that can also be used according to the invention, satisfies the following general formula (VII):

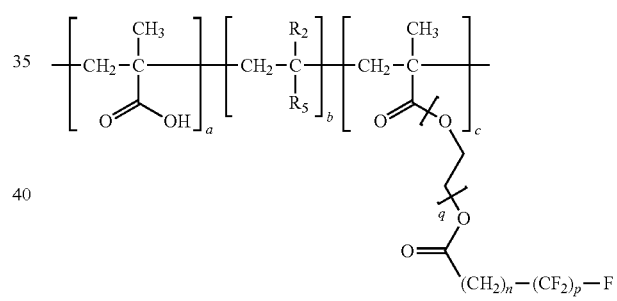

(VII)

in which:
R2 represents a hydrogen atom or a methyl group;
R5 represents [Q]d1-(CH2)$_n$—(CX$_2$)$_p$X in which n is between 1 and 30, d1 is equal to 0 or 1, and Q is equal to —C(O)—O or —C(O)—NH—; and
when X is a hydrogen atom, p is equal to 0;
when X is a fluorine atom, p is between 1 and 12; or R5 represents [Q]d2-α in which:
d2 is equal to 0 or 1;
Q is equal to —C(O)—O or —C(O)—NH—; and
α is equal to —C(CH$_3$)$_3$; —CH(CH$_3$)$_2$; —C(CH$_3$)$_2$—CH$_2$—C(CH$_3$)$_3$; —CN; —CH$_2$CH$_2$—N+(CH$_3$)$_2$CH$_2$CO$_2$); —CH$_2$CH$_2$—NH—C(CH$_3$)$_3$; —CH$_2$CH$_2$—N(CH$_3$)$_2$; pyrrolidinone; caprolactam;
q is a number between 1 and 150;
n is an integer number between 1 and 30;
p is an integer number between 1 and 12;
and in which the indices a and c are integer numbers, that may be identical or different, are greater than or equal to 1, and b is greater than or equal to 0; preferably, a is between 1 and 10,000, b is between 0 and 10,000 and c is between 1 and 5,000.

Also preferably, HASE-F polymers satisfy the following general formula (VIII):

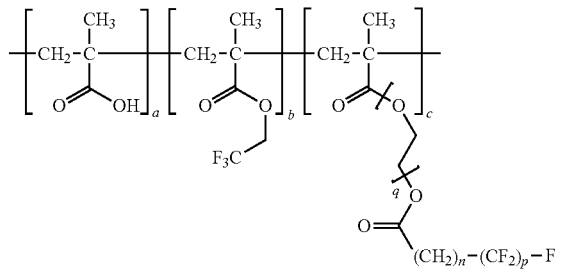
(VIII)

in which:
q is a number between 5 and 10;
n is an integer number between 1 and 30;
p is an integer number between 1 and 12;
a and c are integer numbers that may be identical or different, are greater than or equal to 1, and b is greater than or equal to 0; preferably, a is between 1 and 10,000, b is between 0 and 10,000 and c is between 1 and 5,000.

Even more preferably, the HASE-F polymers satisfy the general formula (VIII) given above in which:
q is equal to 5, 7 or 9;
n is equal to 2;
p is equal to 4, 6 or 8; and
a and c are integer numbers that may be identical or different, are greater than or equal to 1, and b is greater than or equal to 0; preferably, a is between 1 and 10,000, b is between 0 and 10,000 and c is between 1 and 5,000. Even more preferably, the HASE-F polymers satisfying the general formula (VIII) include the following monomers:
from 5 to 85 molar percent of methacrylic acid (AM);
from 1 to 70 molar percent of 2,2,2-trifluoroethyl methacrylate (TFEM); and
from 1 to 50 molar percent of a macromer that is an ester with general formula (IX).

(IX)

in which:
q is equal to 5, 7 or 9; and
p is equal to 4, 6 or 8.

Particularly preferred HASE-F polymers satisfy the formula (VIII) given above, and are such that:
q is equal to 5 and p is equal to 4 (subsequently called a HASE-F-RF4 polymer);
q is equal to 7 and p is equal to 6 (subsequently called a HASE-F-RF6 polymer);
q is equal to 7 and p is equal to 6 (subsequently called a HASE-F-RF8 polymer);

The HASE polymers described above can be synthesised by the same process as that used for ASE polymers. Details of a method of synthesising HASE-H and HASE-F polymers is given in the example 3.

Advantageously, the rheology-modifying or adapting polymers that can be used in compounds according to the invention are chosen:
i) from among non-associative ASE-H polymers with general formula (I) given below:

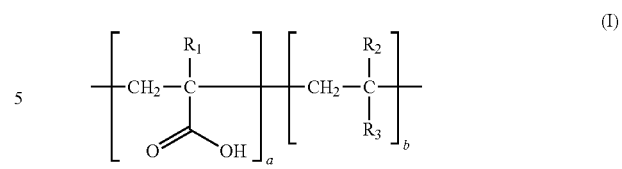
(I)

in which:
R1 and R2 represent a hydrogen atom or a —CH$_3$; methyl group
R3 represents [Q]$_{d1}$-(CH2)$_n$—H in which n is between 1 and 30, d1 is equal to 0 or 1, and Q is equal to —C(O)—O— or —C(O)—NH—;
or
R3 represents [Q]d2-α, in which:
d2 is equal to 0 or 1;
Q is equal to —C(O)—O— or —C(O)—NH—; and
α is equal to —C(CH$_3$)$_3$; —CH(CH$_3$)$_2$; —C(CH$_3$)$_2$—CH$_2$—C(CH$_3$)$_3$; —CN; —CH$_2$CH$_2$—N+(CH$_3$)$_2$ CH$_2$CO$_2^-$); —CH$_2$CH$_2$—NH—C(CH$_3$)$_3$; —CH$_2$CH$_2$—N(CH$_3$)$_2$; pyrrolidinone; caprolactam;
and in which the indices a and b are integer numbers, that may or may not be identical, greater than 1;
or
ii) from among non-associative ASE-F polymers with the following general formula (II):

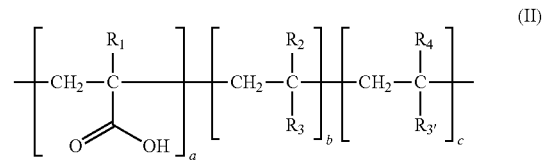
(II)

in which:
R1, R2 and R4 represent a hydrogen atom or a —CH$_3$ methyl group;
R3 represents [Q]$_{d1}$-(CH$_2$)$_n$—H in which n is between 1 and 30, d1 is equal to 0 or 1, and Q is equal to —C(O)—O— or —C(O)—NH—;
or
R3 represents [Q]d2-α in which:
d2 is equal to 0 or 1;
Q is equal to —C(O)—O— or —C(O)—NH—; and
α is equal to —C(CH$_3$)$_3$; —CH(CH$_3$)$_2$; —C(CH$_3$)$_2$—CH$_2$—C(CH$_3$)$_3$; —CN; —CH$_2$CH$_2$—N+(CH$_3$) 2 CH$_2$CO$_2^-$); —CH$_2$CH$_2$—NH—C(CH$_3$)$_3$; —CH$_2$CH$_2$—N(CH$_3$)$_2$; pyrrolidinone; caprolactam;
R3' represents [Q]$_{d1}$-(CH$_2$)$_n$—(CX$_2$)$_p$X in which n is between 1 and 30, d1 is equal to 0 or 1, and Q is equal to —C(O)—O— or —C(O)—NH—, X is a fluorine atom F and p is between 1 and 12;
and in which indices a and c are integer numbers that may be identical or different and are greater than 1 and b is greater than or equal to 0;
or
iii) among HASE associative polymers with macromers with hydrocarbon chain (HASE-H-RH or HASE-F-RH) or fluorocarbon chain (HASE-F-RF) satisfying the following general formula (III):

$$\left[ -CH_2-\underset{\underset{OH}{\overset{\|}{C}}}{\overset{R_1}{\underset{|}{C}}}- \right]_a \left[ -CH_2-\underset{R_5}{\overset{R_2}{\underset{|}{C}}}- \right]_b \left[ -CH_2-\underset{R_7}{\overset{R_6}{\underset{|}{C}}}- \right]_c \quad (III)$$

in which:
R1, R2 and R6 represent a hydrogen atom or a methyl group;
R5 represents $[Q]_{d1}$-$(CH_2)_n$—$(CX_2)_p X$ in which n is between 1 and 30, d1 is equal to 0 or 1, and Q is equal to —C(O)—O or —C(O)—NH—; and
when X is a hydrogen atom, p is equal to 0;
when X is a fluorine atom, p is between 1 and 12;
or
R5 represents $[Q]d2$-α in which:
d2 is equal to 0 or 1;
Q is equal to —C(O)—O or —C(O)—NH—; and
α is equal to —C(CH$_3$)$_3$; —CH(CH$_3$)$_2$; —C(CH$_3$)$_2$—CH$_2$—C(CH$_3$)$_3$; —CN; —CH$_2$CH$_2$—N+(CH$_3$)$_2$ CH$_2$CO$_2^-$); —CH$_2$CH$_2$—NH—C(CH$_3$)$_3$; —CH$_2$CH$_2$—N(CH$_3$)$_2$; pyrrolidinone; caprolactam;
R7 represents -$[Q']_{d3}$-$(OCH_2CH_2)_q$-$[Q'']_{d4}$-$(CH_2)_n(CX_2)_p X$ in which Q' is equal to —CH$_2$, C(O), O—C(O) or —NH—C(O), n is between 1 and 30, q is between 1 and 150, d3 and d4 are equal to 0 and/or 1, Q" is equal to —O—C(O) or —NH—C(O); and
when X is a hydrogen atom, p is equal to 0;
when X is a fluorine atom, p is between 1 and 12;
and in which the indices a and c are integer numbers, identical or different, greater than or equal to 1, and b is greater than or equal to 0.

Particularly advantageously, the rheology-modifying or adapting polymers are chosen from among:
ASE-H polymers that include the following monomers:
from 10 to 20 molar percent of methacrylic acid (AM);
from 80 to 90 molar percent of ethyl acrylate (AE);
or
ASE polymers with hydrocarbon chain (ASE-F) including the following monomers:
from 50 to 60 molar percent of methacrylic acid (AM);
from 5 to 15 molar percent of ethyl acrylate (AE); and
from 30 to 40 molar percent of 2,2,2-trifluoroethyl methacrylate (TFEM);
or
HASE-H-RH polymers that satisfy the general formula (V) and that include:
from 5 to 85 molar percent of methacrylic acid (AM);
from 5 to 60 molar percent of ethyl acrylate (AE); and
from 1 to 90 molar percent of a macromer that is an ester with a general formula (IV) defined above;
or
HASE-F-RH polymers that satisfy the general formula (VI) and that include:
from 30 to 85 molar percent of methacrylic acid (AM);
from 0 to 50 molar percent of 2,2,2-trifluoroethyl methacrylate (TFEM); and
from 1 to 90 molar percent of a macromer that is an ester with general formula (IV).

Even more advantageously, the rheology-modifying or adapting polymers are chosen from among the following polymers:
ASE-H;
ASE-F;
HASE-H-RH4;
HASE-H-RH6;
HASE-H-RH8;
HASE-F-RH4;
HASE-F-RH6;
HASE-F-RH8;
HASE-F-RF4;
HASE-F-RF6;
HASE-F-RF8.

Furthermore, as described in example 4, the Applicant has demonstrated that the viscosity of polymers can be increased by increasing the molar ratio of hydrocarbon or fluorinated macromers in HASE polymers.

Also preferably, the molar percent of macromers in HASE polymers is between 1 and 85 molar percent. More preferably, the molar percent is between 3 and 50 molar percent of macromers.

Even more preferably, the molar percent is 13.5 molar percent of macromers.

Rheology and goniometry characterisation of all polymers has made it possible to demonstrate that HASE-F-RF8 polymers with 3.3%, 13.5% and 45.9 molar percent of macromers were particularly preferred particularly for their oleophobia and the viscosity of their solutions.

Particularly advantageously, the polymer according to the invention is the HASE-F-RF8 polymer, preferably with 13.5 molar percent of macromer.

The compound according to the invention is formed by the covalent association of one or several amine functionalised micro- or nanoparticles as described above, with one or several-rheology modifying polymers as described above.

It is preferable to obtain a homogeneous dispersion of micro- or nanoparticles within the polymer matrix by eliminating all aggregation, to optimise the protective effect against toxins.

Furthermore, since the micro- or nanoparticles are in powder form, they can cause inflammation of lungs by fixing to them (by inhalation) or by entry into the blood (by penetration through the skin). Thus, the Applicant covalently grafted the micro- or nanoparticles to polymers, in order to avoid this type of toxicity and control dispersion. This grafting can be done using the method called the "grafting to" method.

The covalent association of micro- or nanoparticles with polymers may be made by making amine functionalised micro- or nanoparticles react on polymers with carboxylic acid functions (amidation reaction) in the aqueous phase. Micro- or nanoparticles may be grafted on polymers by esterification or amidation.

Grafting is preferably done by amidation that is a reaction with a higher efficiency than esterification because the nucleophilia of nitrogen is higher than that of alcohol.

Examples of grafting amine functionalised micro- or nanoparticles with associative or non-associative polymers are given in example 5.

As described above, before the grafting step, the micro- or nanoparticles of cerium oxide (CeO$_2$) were synthesised and then amine functionalised to react on acid functions of rheology-modifying or adapting polymers.

The covalent bond has many advantages. It firstly prevents penetration of micro or nanoparticles through the respiratory tract but also through the skin into the human or animal body, and also to control the dispersion of micro- or nanoparticles within the matrix in which the micro- or nanoparticles are bonded. In order to achieve this, the polymer or the polymeric matrix contains compounds with functions that can react with the micro- or nanoparticles and that can also be used in a topical treatment.

According to the invention, the micro- or nanoparticles are covalently bonded to a rheology-modifying polymer containing fluorinated monomers firstly to improve the film forming property and secondly to increase hydrophobia and oleophobia so as to "push" toxins away. The objective is also to provide an optimum film forming character for surface protection by means of different polymers, and a more or less strong interaction between micro- or nanoparticles.

Micro- or nanoparticles of cerium dioxide enable destruction by photodegradation of toxins that come into contact with the film before their penetration into the skin or into the support.

Advantageously, according to the invention, nanoparticles are preferred to microparticles. Nanoparticles are chosen due to their large specific surface area compared with microparticles, so as to increase the adsorption efficiency. This micro- or nanoparticulate lattice is dispersible in a basic aqueous medium due to the presence of carboxylic acid in the copolymer and can therefore easily be included in a topical treatment.

The number of cerium oxide ($CeO_2$) equivalent in compounds according to the invention can be varied, in other words the number of amine function equivalents carried by functionalised cerium oxide ($CeO_2$) micro- or nanoparticles compared with the number of acid function equivalents carried by the polymer. A number of cerium oxide equivalents less than or equal to 1 could then give compounds with improved properties, for example dispersion and oleophobia properties.

The polymer/micro- or nanoparticles ratio was calculated by the number of acid function equivalents carried by the polymer as a function of the number of amine function equivalents carried by the micro- or nanoparticles (for 1 acid functions equivalent contained in the polymer, 1 amine functions equivalent was introduced) (in which for 1 acid functions eq, 0.3 amine functions eq added).

Preferably, the number of cerium oxide ($CeO_2$) equivalents in compounds according to the invention is between 0.05 and 1. More preferably, it is between 0.3 and 0.8. Even more preferably, the number of equivalents is 0.13.

A second purpose of the invention is a protective topical treatment comprising a compound according to the invention, in a pharmaceutically and/or cosmetically acceptable medium.

According to one particular embodiment of the invention, the protective topical treatment also comprises one or several detoxifying agents and/or one or several complementary polymers.

The detoxifying agents are non-toxic and are dermatologically acceptable.

Non-limitative examples of detoxifying agents include benzoyl peroxide, zinc peroxide, magnesium monoperoxyphthalate, sodium perborate, sodium percarbonate, potassium permanganate, carbamide peroxide (urea peroxide), calcium peroxide, titanium dioxide, and agents containing sulphur such as N-acetyl cystein, perpropionic acid, magnesium peroxide or neutralising agents such as zinc oxide, complexants such as etidronic acid and its tetrasodium salt, 1-hydroxyethylenediamine acid (1,1-diphosphonic), sodium propionate, magnesium hydroxycarbonate, potassium nitrate and thioglycolic acid.

The percent by mass of these detoxifying agents is preferably between 0.001 and 60% of the total weight of the composition.

Furthermore, the protective topical treatment according to the invention may also include one or several complementary polymers chosen from among polyperfluoromethylisopropyl ether, the copolymer of dimethicone and vinyldimethicone, the copolymer of diethyleneglycol, adipic acid and glycerin, Polysilicone-8 and polyglycerides of oleic/linoleic/linolenic acids, the role of which consists of making the compositions more fluid or more pleasant to be applied. Polyperfluoromethylisopropyl ether is marketed under the trade name Fomblin™ HC.

The dimethicone and vinyldimethicone polymer is marketed particularly under the trade name Silicone Elastomer Blend DC9041™. The copolymer of diethyleneglycol, adipic acid and glycerin is marketed particularly under the trade name Lexorez 100™. Polysilicone-8 is marketed particularly under the trade name Silicones Plus Polymer VS80Dry™. These complementary polymers were introduced in a percentage by mass varying for example from 0.005% to 10% of the total weight of the composition. The dermatological and/or cosmetic composition according to the invention can also contain emollients, softeners, preservatives or perfumes.

Preferably, the topical treatment according to the invention also includes glycerin.

Also preferably, the topical treatment according to the invention includes between 5 and 20% by weight of a compound according to the invention, preferably 13%, and between 1 and 5% of glycerin, preferably 3.7%, of the total weight of the topical treatment.

Protective topical treatments may be in the form of a gel, lotion, oil in water or water in oil emulsion, dispersion, milk, cream, ointment, foam, stick, spray, aerosol or in any other form appropriate for topical application.

Protective topical treatments according to the invention are intended to be applied on the skin, in prevention and prediction of possible contact with toxic chemicals. They are applied in a sufficiently thick layer on the face and on parts of the body that might be exposed to toxic chemicals. Therefore protective topical treatments preferably also contain a protective barrier base and one or several detoxifying agents, so as to delay the penetration of toxic chemicals into the skin and/or secondly to neutralise them before they can reach their action sites in a living organism.

In one particular embodiment of the invention, the compounds according to the invention are added into the BariedermTech™ cream marketed by the Uriage™ company that in particular contains water, the Poly-2p® complex composed of pyrrolidone polymer and biomimetic phosphorylcholine (Poly-2P™) polymer, glycerin and alcohol.

A third purpose of the invention is a compound or a protective topical treatment according to the invention for use as a medicine.

By acting on the skin barrier, the protective compound or topical treatment according to the invention has preventive properties with regard to human or animal afflictions. Thus, the protective compound or topical treatment according to the invention can also be employed as a substance or composition that can be used on human being or animal, in order to correct or modify their physiological functions by applying a pharmacological, immunological or metabolic action. The protective compound or topical treatment according to the invention can be used in applications to human medicine, particularly in dermatology for the prevention of skin irritations or allergies.

A fourth purpose of the invention is a protective compound or topical treatment according to the invention for use in the prevention of irritations or allergies.

For example, irritations may be skin irritations or allergies related to high risk professional practices or do-it-yourself activities.

High risk professional practices include the use of a chemical or biological risk agent, for example in a hospital or military environment.

Do-it-yourself activities include the use of chemicals, for example for painting or mechanical activities, gardening and renovation of furniture.

The fifth purpose of the invention is the use of a protective compound or topical treatment according to the invention for skin protection or skin decontamination, particularly due to biological or chemical risk agents.

The protective compound or topical treatment may also be used for non-therapeutic applications, for example cosmetic applications, in other words it has an application as an epidermic protective barrier against external aggression.

Thus, the invention also relates to the cosmetic use of the protective compound or topical treatment according to the invention, for protection of the skin against toxins in the organophosphates (OPs) family including pesticides (POP) and organophosphate neurotoxins (NOP), and against vesicants such as sulphur or nitrogen yperites, lewisite and phosgene oxime.

Another purpose of the invention is the cosmetic use of the protective compound or topical treatment according to the invention, for protection against UVA and/or UVB ultraviolet radiation from a natural or artificial source.

Alternately, compounds according to the invention can also be used for applications such as:
catalyst;
polishing agent;
agent for ultraviolet filtration;
paints;
glasses;
ceramics;
luminescent materials;
electronics;
gas detectors;
photovoltaic cells;
oxygen buffers (because they store, release and transport oxygen).

Finally, another purpose of the invention is processes for synthesising compounds according to the invention. Such synthesis processes are described in the examples given below.

The preferred preparation process for a compound according to the invention includes steps to:
mix a coupling agent with a catalyst;
add the mix obtained to a solution of rheology-modifying or adapting polymers chosen from among non-associative polymers and associative polymers, in water;
stir the reaction mix;
add functionalised micro or nanoparticles of cerium oxide ($CeO_2$) with a nominal diameter between 5 and 1,500 nm previously dispersed in aqueous phase, to the reaction mix;
purification of the reaction medium by dialysis; and
recover the compound formed by one or several amine functionalised micro- or nanoparticles covalently associated with one or several rheology-modifying polymers.

Preferably, the coupling agent is N-ethyl(3-dimethylaminopropyl)-N'-carbodiimide hydrochloride (EDC) and the catalyst is N-hydroxysuccinimide (NHS).

EXAMPLE 1: SYNTHESIS OF CERIUM OXIDE NANOPARTICLES

Cerium oxide nanoparticles can be synthesised by different methods. Two methods are described below.
i. Synthesis by the co-precipitation method:
A solution of cerium nitrate ($Ce(NO_3)_3 \cdot 6H_2O$) with 1.15 $mol \cdot L^{-1}$ is mixed with a 5 $mol \cdot L^{-1}$ solution of sodium hydroxide at ambient temperature.

A precipitate of cerium hydroxide (III) is then formed instantaneously according to the following reaction:

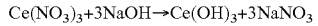

The precipitate of cerium hydroxide (III) obtained is recovered by centrifuging and washing three times with deionised water. A solution of 27% hydrogen peroxide (by mass) is then added at a temperature of 50° C.

Thus, $Ce^{3+}$ ions are oxidised using hydrogen peroxide using the following reaction:

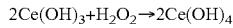

The oxidised precipitate is centrifuged and washed with deionised water and filtered on filter paper and calcinated at 500° C. in air for 6 hours in a porcelain crucible.

The precursor is transformed into cerium oxide by the following reaction:

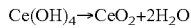

A beige powder is obtained at the end of the experimental procedure. The size of nanoparticles measured by X-ray diffraction and transmission electron microscopy is 9.3 nm and 8.3 nm±2.3, respectively.
ii. Synthesis by Microwaves
100 mL of a 0.5 $mol \cdot L^{-1}$ solution of $(NH_4)_2Ce(NO_3)_6$ is mixed with 100 mL of a 2 $mol \cdot L^{-1}$ sodium hydroxide solution and the mix is then treated by microwaves (Multiwave 3000 Anton Paar). The treatment is summarised in table 1 below. The adjustment parameters are rate 0.5 bars/s, power 1200 W and maximum pressure 10 bars.

TABLE 1 programme for microwave treatment

| Temperature (° C.) | Gradient | Hold time |
|---|---|---|
| 90° C. | 10 minutes | 1 min 30 sec |
| 150° C. | 5 minutes | 15 minutes |
| 20° C. | | 20 minutes |

After centrifuging the precipitate, the result obtained is slightly crystallised cerium oxide with a size of 1.5 to 3 nm. Crystallisation and the size of crystallites can be increased by performing a heat treatment at 400 to 700° C. for 4 hours in air. The crystallites obtained are between 5 and 30 nm.

Cerium oxide nanoparticles are then functionalised by (3-aminopropyl)triethoxysilane in anhydrous toluene with a cerium oxide/amino-silane ratio of 10/1 (FIG. 2).

The amino-silane will react by a condensation reaction with cerium oxide functionalised by —OH groups. It is important to work in an anhydrous medium so that the amino-silane is not hydrolysed, which would cause condensation between hydrolysed Ce—OH groups and different size nanoparticles would be obtained. After the toluene has been eliminated by centrifuging and washing with ethanol, the nanoparticles are stored in an aqueous solution to prevent any contamination through the respiratory tract.

EXAMPLE 2: SUMMARY OF ASE POLYMERS

As shown in FIG. 3, ASE polymers (ASE-H or ASE-F) may for example be composed of methacrylic acid (AM), ethyl acrylate (AE) and/or 2,2,2-trifluoroethyl methacrylate (TFEM).

These polymers can be synthesised by polymerisation in emulsion with sodium dodecyl sulphate (SDS) as surfactant and acetone as co-solvent. Two polymers were synthesised: ASE-H and ASE-F.

Synthesis of a polymer before grafting micro- or nanoparticles can change the polymer chain depending on the application or properties required for the micro- or nanocomposite.

The addition of a fluorinated monomer has a consequence on the stability of the emulsion during polymerisation and an increase in the coagulation phenomenon was observed when the length and quantity of fluorinated monomers increases, causing a reduction in conversion efficiencies. 1% by mass of acetone is used as a co-solvent in order to stabilise the system. This solvent is known to solubilise fluorinated monomers in emulsions. Efficiencies equal to 88 and 51% were obtained for ASE-H and ASE-F polymers after purification by dialysis (4,000-6,000 Da).

It can be seen in table 2 given below that the quantity of methacrylic acid (AM) increases significantly when the fluorinated monomer is added. This is probably due to the less good integration of TFEM during the emulsion process. This can be confirmed by the reduction in the yield of copolymer (51%).

TABLE 2

Composition of ASE-H and ASE-F polymers determined by $^1$H NMR:

| Resonance | No. of protons (nominal) | Intensity | Comp (% mol.) | δH (ppm) | δF (ppm) |
|---|---|---|---|---|---|
| ASE-H | | | | | |
| AM | 1 | 1000 | 17.8 | 12.3 | |
| AE | 2 | 4620.6 | 82.2 | 4.01 | |
| TFEM | 0 | 0 | 0 | | |
| ASE-F | | | | | |
| AM | 1 | 1000 | 55.9 | 12.41 | |
| AE | 2 | 179.8 | 10.0 | 3.96 | |
| TFEM | 2 | 610.5 | 34.1 | | 4.62 |

In table 2 above, AM concerns resonance of the carboxylic acid proton, AE concerns resonance assigned to the methylene proton of ethylic ester and TFEM concerns resonance of the methylene proton of trifluoroethylene ester. The intensity of AM resonance is normalised to 1,000 in each case and intensities are normalised as a function of the nominal number of protons added by resonance.

EXAMPLE 3: SYNTHESIS OF HASE POLYMERS

Figure 4:
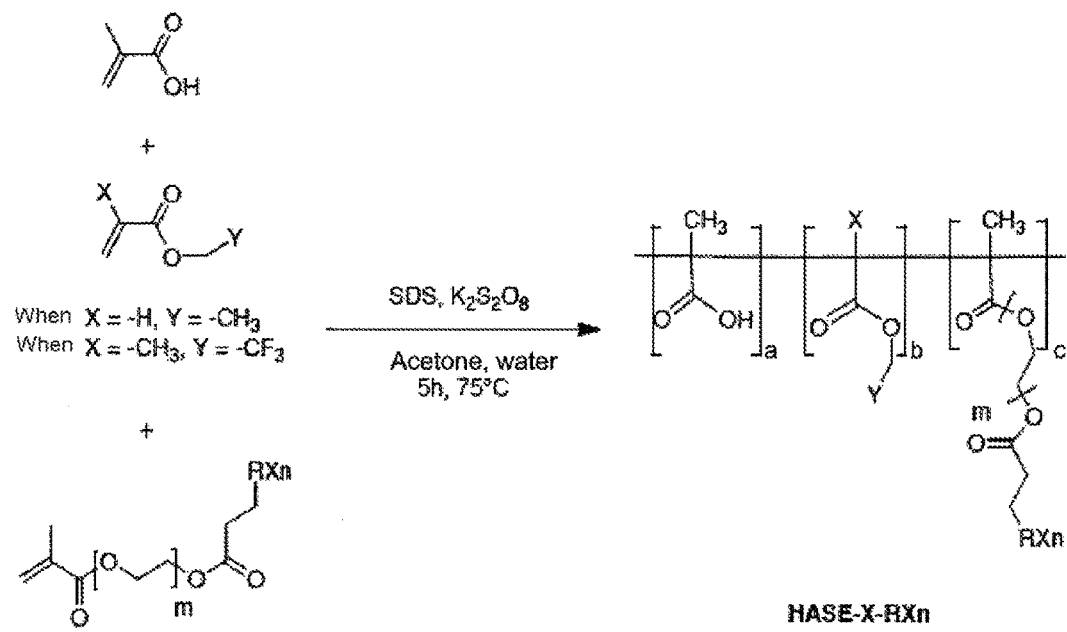
FIG. 4 illustrates a synthesis diagram for HASE associative polymers.

As illustrated in FIG. 4, HASE polymers are synthesised by the same process as ASE polymers. They are composed of methacrylic acid (AM), ethyl acrylate (AE) and/or 2,2,2-trifluoroethyl methacrylate (TFEM) and by a hydrocarbon or fluorinated macromer.

According to FIG. 4, HASE-X-RXn is the reference name of the synthesised polymer.

X corresponds to the letter H if the ethyl acrylate monomer is used. X corresponds to the letter F (HASE-F-RXn) if the fluorinated monomer is used.

RXn varies as a function of the type of hydrocarbon chain (HASE-X-RHn) or fluorinated chain (HASE-X-RFn) and n varies as a function of the number of carbons within the macromer.

Figure 5:
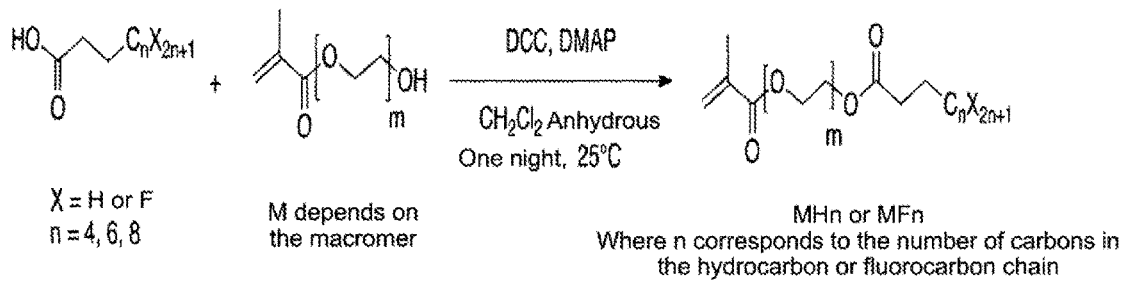
FIG. 5 shows a synthesis diagram for macromers intended to be integrated into HASE associative polymers.

Since the macromers (MHn or MFn) are not commercial products, they were synthesised by an esterification reaction of a polyethylene glycol monomethyl methacrylate on a hydrocarbon or fluorocarbon carboxylic acid compound as illustrated in FIG. 5.

The reaction was catalysed by the use of a coupling agent, N,N'-dicyclohexylcarbodiimide (DCC) in the presence of N,N'-dimethylamino pyridine (DMAP).

The synthesised compounds are obtained with different yields and are characterised by infrared and NMR. The synthesised compounds are listed in table 3 below. The number of PEG monomers, denoted m in FIG. 5, is determined by integration of signals in 1H NMR in chemical displacement ranges of 4.39-4.21 ppm (multiplet) and 3.76-3.64 ppm (multiplet). Since the polyethylene glycol monomethyl methacrylate used initially is commercial and polydispersed, the different monomers were separated on a chromatographic column. The yields of monomers that were used in synthesis of polymers are given in Table 3.

TABLE 3

Summary of chains used, macromer references and reaction yields:

| Chain | Macromer reference (MXn) | Number m in the macromer (determined by $^1$HNMR) | Yield (%) |
|---|---|---|---|
| $C_4H_9$ | MH4 | 7 | 11 |
| $C_6H_{13}$ | MH6 | 7 | 23 |
| $C_8H_{17}$ | MH8 | 9 | 24 |
| $C_4F_9$ | MF4 | 5 | 27 |
| $C_6F_{13}$ | MF6 | 7 | 63 |
| $C_8F_{17}$ | MF8 | 7 | 55 |

The HASE polymers were then synthesised using the same emulsion polymerisation process as the ASE polymers. Therefore, these polymers are synthesised by polymerisation in emulsion with sodium dodecyl sulphate (SDS) as a surfactant and acetone as co-solvent. Two polymers were synthesised: HASE-H and HASE-F. The composition of the polymerisation medium is given in Table 4. The macromer was added with 0.5% by mass.

TABLE 4

Composition of polymers by mass

| Compound (% by mass) | HASE-X-RXn |
|---|---|
| AM | 8.25 |
| AE or TFEM | 10.9 |
| MXn | 0.5 |
| SDS | 1.42 |
| $K_2S_2O_8$ | 0.035 |
| Acetone | 1 |
| Water | 77.9 |

At the end of polymerisation, the polymers obtained with yields varying from 52 to 81%, are purified by dialysis (4,000-6,000 Da) and are then characterised by IR, $^1$H NMR and 19F. The synthesised polymers and the molar composition calculated by 1H NMR are listed in Table 5 below:

TABLE 5

Summary of the main synthesised polymers and their molar composition determined by $^1$H NMR:

| Resonance | No. of protons (nominal) | Intensity | Comp (% mol) |
|---|---|---|---|
| HASE-H-RH4 | | | |
| AM | 1 | 1,000 | 8.5 |
| AE | 2 | 1,071.9 | 9.1 |
| MH4 | 24 | 9,694.9 | 82.4 |
| HASE-H-RH6 | | | |
| AM | 1 | 1,000 | 64.7 |
| AE | 2 | 492 | 31.9 |
| MH6 | 24 | 52.9 | 3.4 |
| HASE-H-RH8 | | | |
| AM | 1 | 1,000 | 51.4 |
| AE | 2 | 921.4 | 47.3 |
| MH6 | 32 | 24.6 | 1.3 |
| HASE-F-RH4 | | | |
| AM | 1 | 1,000 | 78.9 |
| TFEM | 2 | 0 | 0 |
| MH4 | 24 | 266.7 | 21.1 |
| HASE-F-RH6 | | | |
| AM | 1 | 1,000 | 63.1 |
| TFEM | 2 | 482.5 | 30.5 |
| MH4 | 24 | 100.9 | 6.4 |
| HASE-F-RH8 | | | |
| AM | 1 | 1,000 | 69.0 |
| TFEM | 2 | 400.1 | 27.6 |
| MH4 | 32 | 49.4 | 3.4 |
| HASE-F-RF4 | | | |
| AM | 1 | 1,000 | 61.4 |
| TFEM | 2 | 41.6 | 2.6 |
| MF4 | 16 | 586.5 | 36.0 |
| HASE-F-RF6 | | | |
| AM | 1 | 1,000 | 16.0 |
| TFEM | 2 | 4227.6 | 67.4 |
| F6 | 24 | 1041.5 | 16.6 |
| HASE-F-RF8 | | | |
| AM | 1 | 1,000 | 78.2 |
| TFEM | 2 | 236.8 | 18.5 |
| MF4 | 24 | 42.5 | 3.3 |

In table 5 above, AM concerns resonance of the carboxylic acid proton, AE concerns resonance assigned to the methylene proton of ethylic ester, TFEM concerns resonance of the methylene proton of trifluoroethylene ester and MHn concerns the resonance of protons of ethoxylated motifs except the four alpha protons of the two esters. The resonance intensity of AM is normalised to 1,000 in each case and intensities are normalised as a function of the nominal number of protons added by resonance.

Table 5 above also suggests that the MH4 macromer is incorporated into the polymer to a greater extent than others.

The comparison of the different polymer families HASE-H-RHn, HASE-F-RHn and HASE-F-RFn, shows that when the length of the hydrocarbon or fluorocarbon chain forming the macromer increases, the rate of incorporation of the macromer within the polymer reduces.

For the AM, AE and TFEM monomers, no linear variation in the incorporation rate is observed as a function of the type of macromers and the chain length. The DSC analysis determined the vitreous transition temperature(s) of polymers and the CES analysis determined the mass of polymers and their polydispersity index. Two HASE polymers were characterised by CES and the results are given in Table 6 below with polymerisation yields.

TABLE 6

| Polymer | Mw (g·mol$^{-1}$) | M$_w$/Mn | Tg (° C.) | Yield (%) |
|---|---|---|---|---|
| HASE-H-RH8 | 1,162,632 | 4.48 | 54 | 64 |
| HASE-F-RF8 | 593,115 | 1.75 | 63 | 70 |

The differences in molar mass between the hydrocarbon and fluorocarbon polymers can be explained by the fact that the introduction of fluorinated chains destabilises the medium during the polymerisation process that leads to the creation of shorter polymer chains.

EXAMPLE 4: SELECTION OF THE PREFERRED POLYMER AND MODIFICATION TO SAID POLYMER IN ORDER TO OPTIMISE IT a. Selection of the Preferred Polymer:

The different synthesised polymers were analysed in different ways (rheological, dynamic diffusion of light, etc.) including goniometric analyses.

Polymer solutions were spread on a model surface in readiness for the goniometric analyses. 2.5 mg of each polymer was deposited on a glass slide covering about 2-3 cm$^2$ and water was then evaporated in free air. Olive oil drops were deposited on the surfaces, to determine the oleophilia/oleophobia properties of each polymer.

Figure 6:
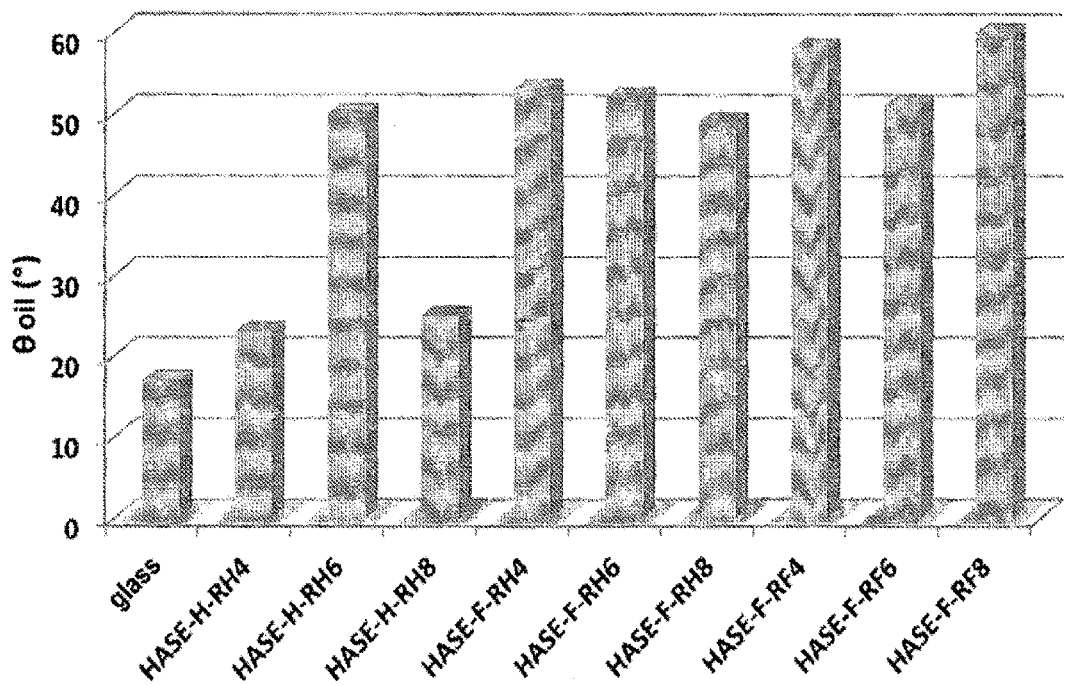
FIG. 6 shows studies of contact angles between olive oil and different polymers previously deposited on a glass slide.

Three 3 µL drops were deposited by a liquid probe to obtain an average. The results of this analysis are shown in FIG. 6 that illustrates contact angles between olive oil and polymers previously deposited on a glass slide.

Olive oil was chosen because the surface tension of this liquid is similar to that of the toxins used for the study ($\gamma=32$ mN/m at 20° C.). Water was not used because the polymer is soluble in water, therefore the film would be solubilised and the contact angle obtained would not be very meaningful.

As shown in FIG. 6, except for HASE-H-RH6, the value of the contact angle increases as soon as a monomer or a fluorocarbon chain is inserted. This is noticeable particularly with the HASE-F-RF8 polymer and its hydrocarbon equivalent for which the contact angles are 660 and 250 respectively. This value also depends on the length of the fluorocarbon chain as can be observed by an increase of 10 to 150 above values for $C_4F_8$ and $C_6F_{13}$ chains when the $C_8F_{17}$ chain is introduced. Also, in comparison with glass alone, a very small quantity of polymer can increase the contact angle with olive oil. It can thus be deduced that the HASE-F-RF8 polymer has a better contact angle (θ=66°) than other polymers.

Considering the various analyses made by grouping rheological and goniometric studies, it was demonstrated that the most viscous polymer in the initial state is the polymer with the best contact angle with olive oil, in other words the HASE-F-RF8 polymer. This latter feature is very important for an application as a protective topical treatment, because the toxin will not bond to or will only very slightly bond to the surface of the topical treatment. In this case, the HASE-F-RF8 polymer was chosen as the preferred polymer for the remainder of the experiments. The HASE-H-RH8 polymer was also studied to perform some analyses and to make a comparison with its fluorocarbon equivalent HASE-F-RF8.

b. Modification to the Preferred Polymer:

Since the HASE-F-RF8 polymer with a molar ratio of macromers equal to 3.3% has attractive surface (in deposition) and rheological properties, the quantity of MF8 macromers was increased to increase the quantity of fluorine chain in the medium. Two other polymers were synthesised for this purpose: one with 13.5 and the other with 45.9 molar percent of macromers. The synthesis pathway is polymerisation in emulsion; the quantity of monomers introduced is given in Table 7 below:

TABLE 7

Composition by mass of monomers introduced during polymerisation

| Compound (% by mass) | HASE-F-RF8 (13.5%) | HASE-F-RF8 (45.9%) |
|---|---|---|
| AM | 6.75 | 8.25 |
| TFEM | 9.9 | 10.9 |
| MF8 | 3 | 0.5 |
| SDS | 1.42 | 1.42 |
| $K_2S_2O_8$ | 0.035 | 0.035 |
| Acetone | 1 | 1 |
| Water | 77.895 | 77.895 |

The molar composition of monomers that are constituents of the polymers deduced by $^{-1}H$ NMR is given in Table 8 below:

TABLE 8

| Resonance | No. of protons (nominal) | Intensity | Comp (% mol.) |
|---|---|---|---|
| HASE-F-RF8 (13.5%) | | | |
| AM | 1 | 1,000 | 41.9 |
| TFEM | 2 | 1,061 | 44.5 |
| MF8 | 24 | 322.5 | 13.5 |
| HASE-F-RF8 (45.9%) | | | |
| AM | 1 | 1,000 | 33.8 |
| TFEM | 2 | 600.6 | 20.3 |
| MF8 | 24 | 1 361.8 | 45.9 |

Figure 7:
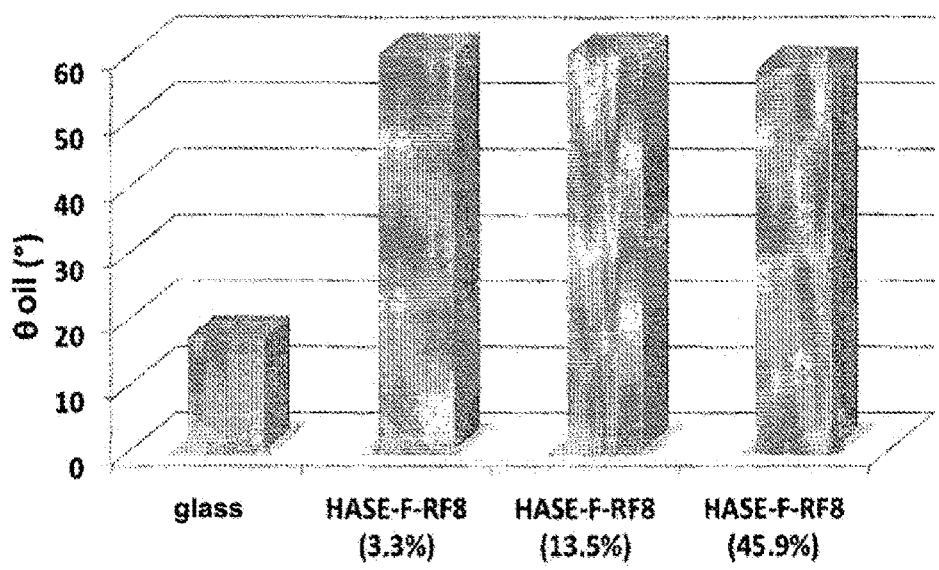
FIG. 7 shows studies of contact angles between olive oil and different HASE-F-RF8 polymers with 3.3; 13.5 and 45.9 molar percent of macromers.
Figure 8:
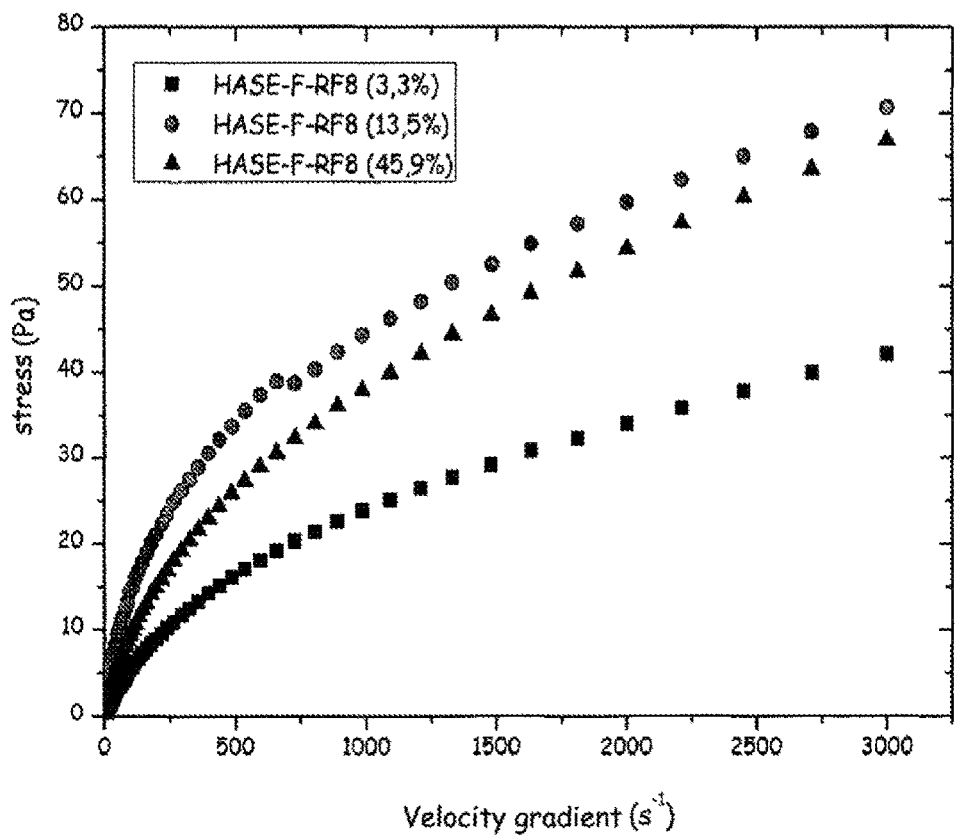
FIG. 8 shows a flow analysis for HASE-F-RF8 polymers (3.3 molar percent of macromer), (13.5 molar percent of macromer) and (45.9 molar percent of macromer)

The goniometry analyses made for these HASE-F-RF8 polymers (13.5 molar percent of macromers) and HASE-F-RF8 polymers (45.9 molar percent of macromers) illustrated in FIG. 7 show that the increase in the macromer content does not change the contact angle for 2.5 mg of deposited polymers. On the other hand, an increase in the macromer content from 3.3 to 13.5 molar percent increases the viscosity of the entire range of velocity gradient as is illustrated in FIG. 8 that shows flow curves for the HASE-F-RF8 polymers (3.3%), (13.5%) and (45.9%).

However, the behaviour of the copolymer with 45.9 molar percent of macromers shows that there is a threshold value starting from which the quantity of macromers no longer improves the rheological properties.

EXAMPLE 5: COUPLING OF CERIUM OXIDE NANOPARTICLES/WITH POLYMER

N-ethyl-(3-dimethylaminopropyl)-N'-carbodiimide (EDC) hydrochloride (0.15 equivalent relative to the quantity of acid functions contained in the polymer) and N-hydroxysuccinimide (NHS) (1/15 equivalent relative to EDC) are mixed and are then added to a polymer solution (1 acid functions equivalent contained in the polymer) in water. The reaction mix is left stirred for one hour at ambient temperature, and then the nanoparticles (0.13 amine functions equivalent relative to acid functions of the polymer) previously dispersed in the aqueous phase are added and the reaction continues for 5 days at ambient temperature. The reaction medium is then purified by dialysis (MWCO: 4,000-6,000 Da). The product obtained is called HASE-F-RF8 (13.5%)/Ce.

EXAMPLE 6: INTRODUCTION OF POLYMER COMPOUNDS/NANOPARTICLES IN CREAM AND GEL TYPE COSMETIC FORMULATIONS a. Formulation in a Cream:

The compounds were introduced in the BariedermTech™ cream marketed by the Uriage™ company.

The products were concentrated and then introduced into the cream cold with 10% by mass and pH=9. The pH chosen is relatively high compared with the pH of the skin (pH f 5) and it is important not to aggress it with a basic cream (risk of damage to the skin) but the chosen compounds have the best properties at about pH=9. The tested compounds formulated in these creams were HASE-F-RF8 (3.3 molar percent of macromers)/Si (0.3 eq); HASE-F-RF8 (13.5 molar percent of macromers)/Si (0.3 eq); HASE-F-RF8 (3.3 molar percent of macromers)/$TiO_2$ (0.3 eq); HASE-F-RF8 (3.3 molar percent of macromers)/$CeO2$ (0.02 eq).

b. Formulation in a Gel:

Two types of gels were synthesised, a hydrophilic gel and a hydrophobic gel.

Details of the gel formulations are given in Table 10 below:

TABLE 10

| Hydrophilic gel | | Hydrophobic gel | |
|---|---|---|---|
| Compound | Gel (% by mass) | Compound | Gel (% by mass) |
| Water | 67.80 | HASE-F-RF8 (13.5%) | 1 |
| Carbopol ™ Ultrez 10 | 0.70 | Polymer/ nanoparticles | 2.4 |
| EtOH (96%) | 30.00 | Water | 59.6 |
| TEA (99%) (50% in sol.) | 1.40 | EtOH (96%) | 25 |
| Polymer/ nanoparticle | 0.10 | TEA (99%) (50% in sol.) | 2 |
| | | Fomblin ™ | 10 |

Fomblin™ is a perfluoropolyether (perfluorinated oil) that performs two roles. The first role is to increase hydrophobia and oleophobia in the medium and the second role is to fluidify the gel. This second property was very useful because the gel becomes elastic at a high polymer content, and will not spread properly. The formula given in Table 10 above is the formula that gives a viscous gel that spreads well on the skin with a pH of between 7.30 and 7.50.

The most attractive gels with the best spreading properties are those containing the following compounds:

HASE-F-RF8 (13.5 molar percent of macromers)/Ce (0.13 eq), and

HASE-F-RF8 (13.5%)/Si (0.3 eq).

Therefore, the Applicant studied the influence of polymer/nanoparticles compounds and Fomblin™ in the hydrophobic gel.

This was done by formulating a gel without these two compounds (white gel), a gel with the HASE-F-RF8 compound (13.5 molar percent of macromers)/Ce (0.13 eq) (gel 2) and a gel with Fomblin™ and the HASE-F-RF8 compound (13.5 molar percent of macromers)/Ce (0.13 eq) (gel 3). The formulas are summarised in the following table 11:

TABLE 11

| White gel | Gel 2 (without Fomblin ™) | Gel 3 (with Fomblin ™) |
|---|---|---|
| HASE-F-RF8 (13.5%) 1% | HASE-F-RF8 (13.5%) 1% | HASE-F-RF8 (13.5%) 1% |
| — | HASE-F-RF8 (13.5%)/ Ce (0.13 eq) 2.4% | HASE-F-RF8 (13.5%)/ Ce (0.13 eq) 2.4% |
| $H_2O$ - 64.4% | $H_2O$ - 62% | $H_2O$ - 59.6% |
| EtOH (96%) 33.1% | EtOH (96%) 30% | EtOH (96%) 25% |
| TEA 99% (50% sol.) 1.7% | TEA 99% (50% sol.) 4.6% | TEA 99% (50% sol.) 4% |
| — | — | Fomblin ™ - 10% |

50 mg (~5 mg/cm$^2$) of each gel (gels 1, 2 and 3) was deposited on a 9-10 cm$^2$ silicone membrane with a Parafilm™ glove finger, to make a better comparison between the effects of differences products. The olive oil deposit was made 20 minutes after spreading the topical treatments and measurements were made one minute after depositing the drop. The white gel and the gel 2 were difficult to spread because their behaviour was elastic. This is not the case for gel 3, which illustrates the fluidising properties of Fomblin™.

These experiments show that the white gel is oleophilic and that its contact angle is smaller than it is for the membrane alone. Unlike gel 2 in which the polymer/nanoparticles compound was introduced, it is seen that the contact angle increases. Therefore the polymer/nanoparticle compound has a positive influence because it reduces the oleophilia of the gel. Finally, the addition of Fomblin™ can give an almost oleophobic gel and shows its influence on oleophobia and also its protective effect.

EXAMPLE 7: EFFICIENCY TEST OF THE PURE PRODUCT

The purpose of this experiment is to determine the protective potential of a protective topical treatment according to the invention by a penetration rate on semi-permeable membranes, against organophosphate compounds such as ethyl O-ethyl-O-(nitro-4-phenyl) phosphonate (paraoxon or POX).

Test on Synthetic Membrane:

The synthetic membrane used is a 400±100 µm thick silicone membrane (polydimethylsiloxane) marketed by the Samco Silicone Products company (Nuneaton, UK).

The membrane is cut in the form of approximately 10 cm$^2$ disks. The penetration test was done on static Franz type diffusion cells made of glass (cells made by a glass manufacturer; Laboratoires VERRE LABO-MULA, Corbas, France). The receiving medium is filled with "Hank's Balance Salt Solution" (HBSS) solution.

TABLE 12

Distribution of membranes relative to products

| Product | Number of membranes |
|---|---|
| Standard (not treated) | 3 |
| HASE-F-RF8 (13.5%) | 4 |
| HASE-F-RF8 (13.5%)/Ce | 6 |

Treatment:

The protective topical treatment according to the invention is applied at 5 mg/cm$^2$ spread using a flexible silicone spatula.

The membrane is then deposited on the receiving compartment. A Teflon™ seal is added onto the membrane and the cell is then closed by the donor compartment, leaving an exposed membrane area equal to 1.13 cm$^2$. When the cell is closed, it is put on a cell-holder placed in a warming bath, and a screw is then added in order to provide good contact between the membrane and the receiving medium. Finally, the membrane and the gel are held at an equilibrium temperature for 20 minutes. The warming bath is set to 38° C. so as to obtain a temperature of 32° C.±1° C. on the membrane surface.

The toxin is deposited at the centre of the membrane in the form of a drop. The quantity of paraoxon (POX) deposited is 5 mg/cm$^2$ namely 4.9 µL.

400 µL samples are taken in the sampling elbow once every one hour 30 minutes for POX. Once the samples have been taken, an identical volume of HBSS is added to keep the quantity of the receiving medium constant. All samples were kept in the freezer at −20° C.

Analysis of the Quantity of POX in the Receiving Medium:

The method used is an enzymatic analysis of the toxin. This analysis method is an indirect method to analyse the activity of an enzyme in the presence of paraoxon (POX). The concentration of paraoxon in the sample is determined based on a clearly defined concentration range and is proportional to the degree of inhibition of the enzyme (butyrylcholinesterase) that was added in a known quantity in each sample.

Figure 9:
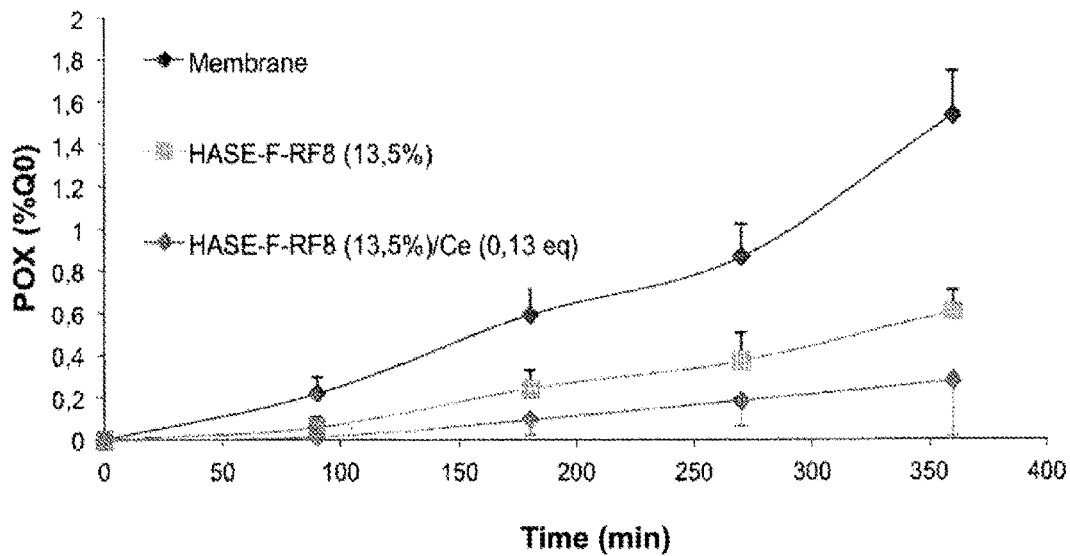
FIG. 9 shows an evaluation study of HASE-F-RF8 (13.5 molar percent of macromer)/Ce and HASE-F-RF8 (13.5 molar percent of macromer) topical treatments against transmembrane penetration of paraoxon.

The results are shown in FIG. 9 that shows the evaluation of the product regarding transmembrane penetration of paraoxon. Q0 represents the percentage of the absorbed dose of paraoxon.

It can be seen that the transmembrane penetration of paraoxon is slowed and reduced slightly when the membrane is pretreated with the HASE-F-RF8 polymer (13.5 molar percent of macromers) and even more with the HASE-F-RF8 compound (13.5 molar percent of macromers)/Ce.

The different products were compared with each other by carrying out a non-parametric Kruskal-Wallis statistical test that compares variances of more than two independent samples at t=6 h, followed by a Dunn test that compares one sample with another, to draw conclusions about the protective effect of the compounds. The polymer does not have a significant protective effect, however the polymer/cerium oxide compound has a significant protective effect on the membrane and the polymer alone.

This illustrates the protective effect of the synthesised fluorocarbon/micro- or nanoparticle polymer compound on transmembrane penetration of POX.

Figure 10:
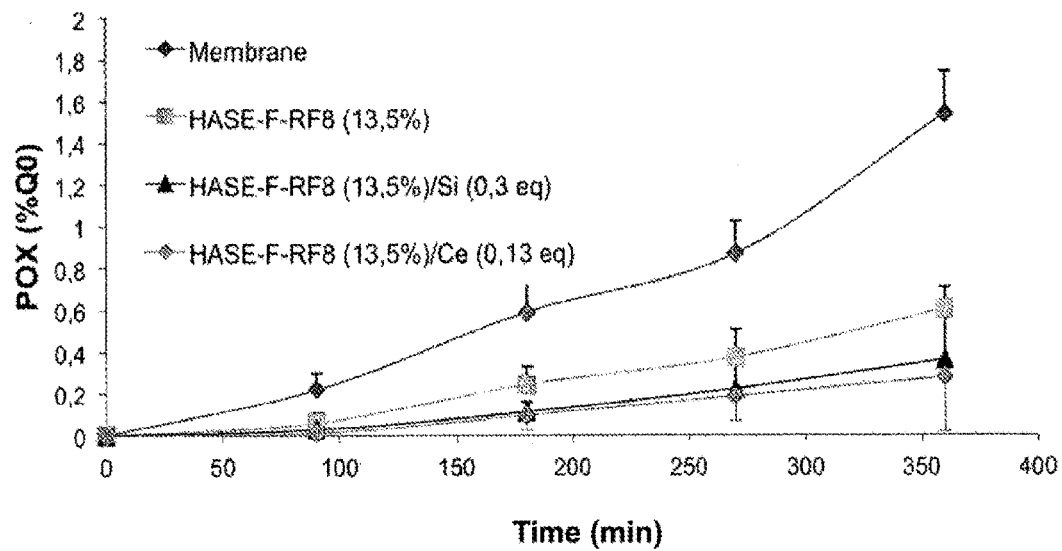
FIG. 10 shows an evaluation study of HASE-F-RF8 (13.5 molar percent of macromer)/Si, HASE-F-RF8 (13.5 molar percent of macromer)/Ce and HASE-F-RF8 (13.5 molar percent of macromer) against transmembrane penetration of paraoxon.

By comparison with the polymer/silica nanoparticles compound (FIG. 10), it is found that there is no significant difference between the protective effects of the HASE-F-RF8 (13.5%)/Ce and HASE-F-RF8 (13.5%)/

(non-parametric Kruskal-Wallis statistical test followed by a Dunn test). This is despite the fact that the efficiency of the HASE-F-RF8 (13.5%)/Ce compound is slightly higher than the compound with HASE-F-RF8 (13.5%)/Si.

By replacing silica nanoparticles with cerium oxide nanoparticles, the compound has the same protective efficiency but does not have the toxicity of silica nanoparticles.

EXAMPLE 8: EXAMPLE OF COMPOUNDS ACCORDING TO THE INVENTION

Figure 11:
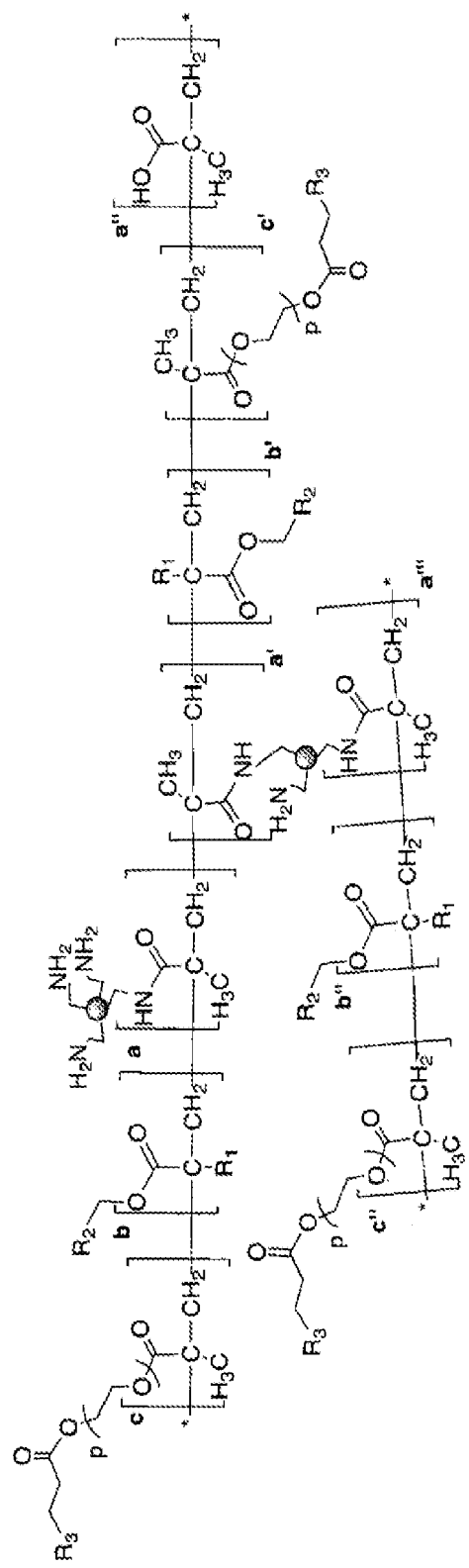
FIG. 11 shows a possible general structure of a compound according to the invention capable of providing a new technology protection.

FIG. 11 shows a general diagram of compounds according to the invention, to obtain a new technology protection. In the diagram in FIG. 11:

- $R_1$ groups correspond for example to hydrogen atoms or alkyl groups with 1 to 4 carbon atoms;
- $R_2$ groups correspond to $C_nX_{n+1}$ groups where X represents a hydrogen or fluorine atom and n is between 1 and 9;
- $R_3$ groups correspond to a hydrocarbon or fluorocarbon chain $C_nX_{n+1}$ in which X represents a hydrogen or fluorine atom and n is between 4 and 8;
- a, a', a'', a''', b, b', b'', c, c' and c'' may be identical or different, are integer numbers greater than 1; and
- the balls or circles represent micro- or nanoparticles of cerium oxide ($CeO_2$) with a nominal diameter between 1 and 1,500 nm.

EXAMPLE 9: INTRODUCTION OF POLYMER COMPOUNDS/NANOPARTICLES INTO COSMETIC FORMULATIONS AND TEST OF THE EFFICIENCY OF SAID FORMULATIONS

The following percentages are expressed as a percentage by weight of the total weight of the formulation.

a. Formulation:

(i) Active constituents:

Active constituents are compounds according to the invention, in other words cerium oxide grafted polymers, with at least 9% integrated into the formulations.

(ii) Ingredients:

Ingredients are particularly film-forming agents and skin tensor agents. They are selected after studying their compatibility with the polymer, their oleophobic/oleophilic potential and their usage protocol (% and integration).

Active constituents are integrated in distilled water (aqueous phase) and are stirred for one night using a magnetised bar and a stirring plate.

The formulas are neutralised on the next day to pH 7 using 1N soda. Ingredients are then added by stirring by hand with a spatula.

The film-forming effect and the homogeneity of the formulas is verified after formulation.

200 mg of the formulas was spread on a glass slide (10 cm²) and a silicone membrane (7.3 cm²) and the slides were allowed to dry between 4 h and one night (about 12 hours).

Visual and microscope observations were then made to observe the film-forming effect of ingredients (no crazing of formulas) and the homogeneity.

The film-forming and homogeneous formulas were then tested for their efficiency.

Table 13 below shows the main preparation steps and the different components of a formulation according to the invention called "CM14":

TABLE 13

| Name | mass (g) | % | Protocol |
|---|---|---|---|
| MIX 1 (D and D + 1) | | | |
| Polymer-Ce (ref CB28) | 3.0077 | 16.2 | Mix and stir 1 night |
| Distilled water | 9.019 | 48.5 | |
| 1N soda | 6.5506 | 35.3 | D + 1: neutralisation to pH |
| TOTAL | 18.58 | 100 | |
| MIX 2 (D + 1) | | | |
| Mix 1 (P—Ce 16.2%, Water 48.5%, 1N Soda 35.3%) | 5.1193 | 80.5 | D + 1 mix by hand |
| Glycerin | 0.2352 | 3.7 | |
| Distilled water | 1.0067 | 15.8 | water added to top up |
| TOTAL | 6.36 | 100 | (pH real D + 9: 6.7 at 21.3°) |

| Detail of the CM 14 formulation obtained | | |
|---|---|---|
| Name | mass (g) | % |
| Mix 1 | 5.1193 | |
| P—Ce 16.2% | 0.8288 | 13.0 |
| Water 48.5% | 2.4853 | 39.1 |
| 1N soda 35.3% | 1.8051 | 28.4 |
| Distilled water | 1.0067 | 15.8 |
| Glycerin | 0.2352 | 3.7 |
| TOTAL | 6.3612 | 100 |

The "CM14" formulation finally contains 13% of polymer-cerium oxide, 3.7% glycerin, 28.4% of 1N soda and the remainder (namely 54.9%) is distilled water. Deposits are homogeneous and film forming.

B. Efficiency Tests:

Tests were carried out on silicone membranes (7.3 cm²) mounted on Franz cells. About 200 mg of each formula is applied (27 mg/cm²) and dried (about 1 to 3 hours). After complete drying, the membranes are mounted in Franz cells (HBSS receiving medium) and 4.9 µl of paraoxon is applied at the centre. 400 µl of the receiving medium is taken once every hour, for six hours. Furthermore, the quantities remaining on the surface and in the formula are also recovered after 6 hours ($T_{final}$).

The accumulated quantity of recovered toxin is expressed as a percentage of the applied initial dose (% Q0) and its variation is shown graphically as a function of time. The maximum absorption rate or maximum flux (Jmax) is given by the slope of the curve (the trend line) obtained when the penetration rate becomes constant and maximum. The intersection of this slope with the abscissa is equal to the latency time ($\lambda$).

The formulas (tests) are compared with control membranes (without protection) in the experiment (a control is made for each test). The number of replicas is fixed at n=3 for the first tests, and an efficient cream must be validated on n=6.

Ideally, a barrier cream is considered to be efficient if the time for penetration of the toxin through the skin is increased (longer latency time $\lambda$) and if the penetration rate is lower (shorter Jmax).

Figure 12:
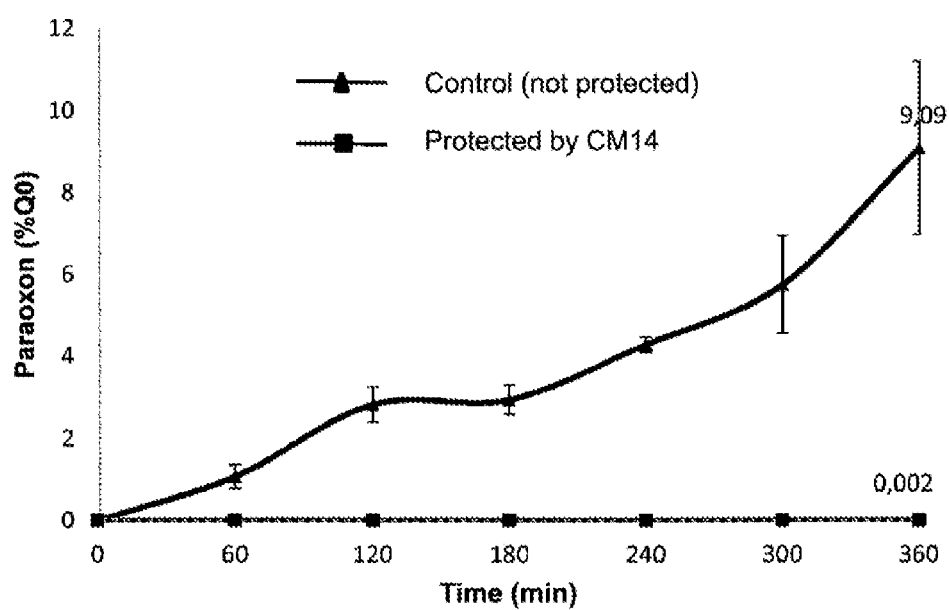
FIG. 12 shows an evaluation study of the efficiency of a formulation comprising a compound according to the invention regarding transmembrane penetration of paraoxon.

As illustrated in FIG. 12, the Applicant has demonstrated that the CM14 formulation significantly reduces the penetration of paraoxon.

The main penetration parameters are given in table 14 below.

TABLE 14

| Parameters | Control | CM14 | CM14/control |
|---|---|---|---|
| Jmax ($\mu g/cm^2/min$) | 0.26 ± 0.07 | <0.01 | >26 |
| λ (min) | 4 ± 1 | | |

These experiments particularly show that:
(1) The maximum flux is 26 times lower;
(2) The latency time can no longer be measured for CM14 (point<3 for the trend line); and
(3) The quantity at T=6 h is significantly reduced (9.09% Q0 compared with <0.01% Q0).

Thus, the CM14 formulation comprising 13% of the polymer-cerium oxide compound according to the invention, combined with 3.7% glycerin can give a formulation with a homogeneous and film-forming deposit in which the protective properties of polymer-cerium oxide active constituents are maintained.

The invention claimed is:

1. A compound formed by amine functionalised micro- or nanoparticles associated covalently with rheology-modifying or adapting polymers, wherein:
   the functionalised micro- or nanoparticles are amine functionalised micro- or nanoparticles of cerium oxide $CeO_2$, having a diameter between 1 and 1,500 nm;
   the rheology-modifying or adapting polymers are chosen from among non-associative or associative polymers;
   the micro- or nanoparticles are grafted on the polymers by amidation,
      wherein the micro- or nanoparticles of cerium oxide are amine functionalised by (3-aminopropyl)triethoxysilane.

2. The compound according to claim 1, wherein the rheology-modifying or adapting polymers are chosen from among:
   non-associative ASE-H polymers with the following general formula (I)

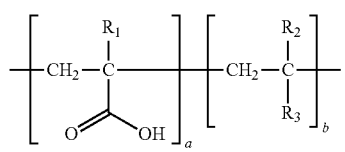

(I)

in which:
   R1 and R2 represent a hydrogen atom or a —$CH_3$ methyl group;
   R3 represents $[Q]_{d1}$-$(CH_2)_n$—H in which n is between 1 and 30, d1 is equal to 0 or 1, and Q is equal to —C(O)—O or —C(O)—NH—;
or
R3 represents $[Q]d2$-α, in which:
   d2 is equal to 0 or 1;
   Q is equal to —C(O)—O or —C(O)—NH—; and
   α is equal to —$C(CH_3)_3$; —$CH(CH_3)_2$; —$C(CH_3)_2$—$CH_2$—$C(CH_3)_3$; —CN; —$CH_2CH_2$—N+$(CH_3)_2$ ($CH_2CO_2^-$); —$CH_2CH_2$—NH—$C(CH_3)_3$;

—$CH_2CH_2$—N$(CH_3)_2$; pyrrolidinone; caprolactam; and in which indices a and b are integer numbers that may be identical or different, and are more than 1;
or
from among non-associative ASE-F polymers with the following general formula (II)

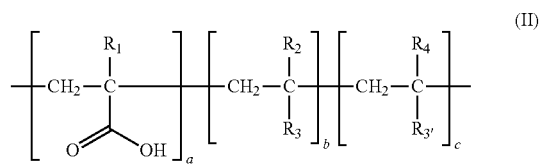

(II)

in which:
   R1, R2 and R4 represent a hydrogen atom or a —$CH_3$ methyl group;
   R3 represents $[Q]_{d1}(CH_2)_n$—H in which n is between 1 and 30, d1 is equal to 0 or 1, and Q is equal to —C(O)—O or —C(O)—NH—;
or
R3 represents $[Q]d2$-α, in which:
   d2 is equal to 0 or 1;
   Q is equal to —C(O)—O or —C(O)—NH—; and
   α is equal to —$C(CH_3)_3$; —$CH(CH_3)_2$; —$C(CH_3)_2$—$CH_2$—$C(CH_3)_3$; —CN; —$CH_2CH_2$—N+$(CH_3)_2$ ($CH_2CO_2^-$); —$CH_2CH_2$—NH—$C(CH_3)_3$; —$CH_2CH_2$—N$(CH_3)_2$; pyrrolidinone; caprolactam;
   R3' represents $[Q]_{d1}$-$(CH_2)_n$—$(CX_2)_p$X in which n is between 1 and 30, d1 is equal to 0 or 1, and Q is equal to —C(O)—O or —C(O)—NH—, X is a fluorine atom F and p is between 1 and 12;
and in which the indices a and c are integer numbers, identical or different, greater than 1 and b is greater than or equal to 0;
or
from among associative HASE polymers with hydrocarbon (HASE-H-RH or HASE-F-RH) or fluorocarbon (HASE-F-RF) chain satisfying the following general formula (III):

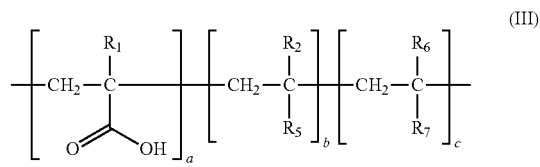

(III)

in which:
   R1, R2 and R6 represent a hydrogen atom or a methyl group;
   R5 represents $[Q]_{d1}$-$(CH_2)_n$—$(CX_2)_p$X in which n is between 1 and 30, d1 is equal to 0 or 1, and Q is equal to —C(O)—O or —C(O)—NH—; and
   when X is a hydrogen atom, p is equal to 0;
   when X is a fluorine atom, p is between 1 and 12;
or
R6 represents $[Q]d2$-α in which:
   d2 is equal to 0 or 1;
   Q is equal to —C(O)—O or —C(O)—NH—; and
   α is equal to —$C(CH_3)_3$; —$CH(CH_3)_2$; —$C(CH_3)_2$—$CH_2$—$C(CH_3)_3$; —CN; —$CH_2CH_2$—N+$(CH_3)_2$ ($CH_2CO_2^-$); —$CH_2CH_2$—NH—$C(CH_3)_3$; —$CH_2CH_2$—N$(CH_3)_2$; pyrrolidinone; caprolactam;

R7 represents -[Q']$_{d3}$-(OCH$_2$CH$_2$)$_q$-[Q'']$_{d4}$-(CH$_2$)$_n$(CX$_2$)$_p$X in which Q' is equal to —CH$_2$, C(O), O—C(O) or —NH—C(O), n is between 1 and 30, q is between 1 and 150, d3 and d4 are equal to 0 and/or 1, Q'' is equal to —O—C(O) or —NH—C(O); and when X is a hydrogen atom, p is equal to 0;

when X is a fluorine atom, p is between 1 and 12;

and in which the indices a and c are integer numbers, identical or different, greater than or equal to 1, and b is greater than or equal to 0.

3. The compound according to claim 2, wherein rheology-modifying or adapting polymers are chosen from among:

ASE-H;
ASE-F;
HASE-H-RH4;
HASE-H-RH6;
HASE-H-RH8;
HASE-F-RH4;
HASE-F-RH6;
HASE-F-RH8;
HASE-F-RF4;
HASE-F-RF6; or
HASE-F-RF8.

4. A protective topical treatment composition comprising a compound according to claim 1, in a pharmaceutically and/or cosmetically acceptable medium.

5. The protective topical treatment composition according to claim 4, further comprising one or several detoxifying agents and/or one or several complementary polymers.

6. The protective topical treatment composition according to claim 4, further comprising glycerin.

7. The protective topical treatment composition according to claim 6, comprising between 5 and 20% of the compound and between 1 and 5% glycerin, by weight of the total weight of the topical treatment composition.

8. The protective topical treatment composition according to claim 7, comprising 13% of the compound and 3.7% of glycerin, by weight of the total weight of the topical treatment.

9. A medicinal composition comprising the compound according to claim 1.

10. The medicinal composition according to claim 9, which is effective in prevention of skin irritations or allergies.

11. The compound according to claim 1, which is effective in skin protection or decontamination due to biological or chemical risk agents.

12. A protective topical treatment composition comprising the compound according to claim 2, in a pharmaceutically and/or cosmetically acceptable medium.

13. A protective topical treatment composition comprising the compound according to claim 3, in a pharmaceutically and/or cosmetically acceptable medium.

14. The protective topical treatment composition according to claim 12, further comprising one or several detoxifying agents and/or one or several complementary polymers.

15. The protective topical treatment composition according to claim 13, further comprising one or several detoxifying agents and/or one or several complementary polymers.

16. The protective topical treatment composition according to claim 12, further comprising glycerin.

17. The protective topical treatment composition according to claim 13, further comprising glycerin.

18. The compound according to claim 3, wherein the rheology-modifying or adapting polymers are HASE-F-RF8.

19. The compound according to claim 1, wherein the amine functionalised micro- or nanoparticles are grafted on the polymers by reaction of amine groups of the micro- or nanoparticles with acid groups of the polymers.

* * * * *